United States Patent
Milestone et al.

(10) Patent No.: US 9,394,211 B2
(45) Date of Patent: *Jul. 19, 2016

(54) PROCESS FOR REFINING CHEMICALS FROM PULP AND PAPER MILL WASTEWATERS

(71) Applicant: HER MAJESTY THE QUEEN IN RIGHT OF CANADA, AS REPRESENTED BY THE MINISTER OF ENVIRONMENT, Gatineau (CA)

(72) Inventors: Craig Brennan Milestone, Toronto (CA); Deborah L. MacLatchy, Waterloo (CA); L. Mark Hewitt, Burlington (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/639,662

(22) Filed: Mar. 5, 2015

(65) Prior Publication Data

US 2015/0322627 A1 Nov. 12, 2015

Related U.S. Application Data

(63) Continuation of application No. 13/639,539, filed as application No. PCT/CA2011/000388 on Apr. 7, 2011, now Pat. No. 8,993,809.

(60) Provisional application No. 61/321,582, filed on Apr. 7, 2010.

(51) Int. Cl.

| | | |
|---|---|---|
| C07C 45/00 | (2006.01) | |
| C07C 29/00 | (2006.01) | |
| C07C 41/00 | (2006.01) | |
| C07B 63/00 | (2006.01) | |
| B01D 11/04 | (2006.01) | |
| C07C 7/12 | (2006.01) | |
| C07C 29/76 | (2006.01) | |
| C07C 41/36 | (2006.01) | |
| C07C 45/79 | (2006.01) | |
| B01D 11/00 | (2006.01) | |
| C02F 1/00 | (2006.01) | |
| D21C 11/00 | (2006.01) | |
| B01D 61/02 | (2006.01) | |
| B01D 61/00 | (2006.01) | |
| C02F 1/44 | (2006.01) | |
| C02F 103/28 | (2006.01) | |

(52) U.S. Cl.
CPC ............... C07B 63/00 (2013.01); B01D 11/00 (2013.01); B01D 11/0426 (2013.01); B01D 11/0492 (2013.01); B01D 61/00 (2013.01); B01D 61/025 (2013.01); C02F 1/00 (2013.01); C02F 1/441 (2013.01); C07C 7/12 (2013.01); C07C 29/76 (2013.01); C07C 41/36 (2013.01); C07C 45/79 (2013.01); D21C 11/00 (2013.01); D21C 11/0007 (2013.01); B01D 2311/08 (2013.01); B01D 2311/18 (2013.01); B01D 2311/2626 (2013.01); B01D 2311/2649 (2013.01); B01D 2311/2676 (2013.01); C02F 2103/28 (2013.01)

(58) Field of Classification Search
CPC .......... C07C 45/79; C07C 29/76; C07C 41/36
USPC .......................... 568/438, 638, 653, 819, 875
See application file for complete search history.

(56) References Cited

U.S. PATENT DOCUMENTS 6,110,376 A 8/2000 Savage et al.

OTHER PUBLICATIONS

Belknap et al., Environmental Toxicology and Chemistry, 25(9):2322-2333 (2006). "Identification of compounds associated with testosterone depression in fish exposed to bleached kraft pulp and paper mill chemical recovery condensates."
Dube et al., Environmental Toxicology and Chemistry, 20(5):985-995 (2001). "Identification and treatment of a waste stream at a bleached-kraft pulp mill that depresses a sex steroid in the Mummichog (*Fundulus heteroclitus*)."
Hewitt et al., Environmental Toxicology and Chemistry, 21(7):1359-1367 (2002). "Isolation of compounds from bleached kraft mill recovery condensates associated with reduced levels of testosterone in Mummichog (*Fundulus heteroclitus*)."
MacLatchy et al., TAPPI International Environmental, Health and Safety Conference and Exhibit, Charlotte, NC, USA, Apr. 22-25, 2001, pp. 459-472. "Evaluating reverse osmosis treatment for removal of compounds from recovery condensates at a bleached kraft mill tht affect fish hormone control."
Hewitt et al., Environmental Toxicology and Chemistry, 27(3):682-697 (2008); Altered Reportuction in Fish Exposed to Pulp and Paper Mill Effluents: Roles of Individual Compounds and Mill Operating Conditions.

*Primary Examiner* — Sikarl Witherspoon

(57) ABSTRACT

A process for isolating at least one target compound, such as manool, geranyl linalool, ethyl guaiacol, eugenol, veratraldehyde, squalene, terpin, cholesterol, beta-sitosterol, campesterol, stigmasterol, stigmastenol and dehydroabietic acid, from biomass, the process including steps of: obtaining a condensate from a recovery evaporator, a reverse osmosis retentate of a condensate of a pulp and paper mill, or both, the condensate, retentate or both being substantially free of higher molecular weight (approximately >1000 Da) cellulose and/or lignin and/or lignin-derived material; optionally pH adjusting and filtering the condensate to collect insoluble material; extracting the condensate, the collected insoluble material, or both, with solid phase extraction (SPE), liquid-liquid extraction or solid-liquid extraction to produce an extract containing the at least one target compound; and optionally purifying the extract containing the at least one target compound by thermal fractionation, chromatographic separation, recrystallization ion exchange, chelation, adsorption/desorption, lyophilization and sublimation or combinations thereof. The method is particularly useful for isolating the target compounds from wastewaters produced in a kraft pulp and paper mill, especially from recovery evaporator condensates produced during the treatment of black liquor.

20 Claims, 17 Drawing Sheets

PROCESS FOR REFINING CHEMICALS FROM PULP AND PAPER MILL WASTEWATERS

CROSS-REFERENCE TO RELATED APPLICATIONS

This application is a continuation application that claims benefit under 35 USC §120 of a U.S. application Ser. No. 13/639,539, filed on Dec. 6, 2012 now U.S. Pat. No. 8,993,809 issued Mar. 31, 2015, which is a 35 U.S.C. §371 National Phase Entry Application of International Application No. PCT/CA2011/000388 filed Apr. 7, 2011, which designates the U.S., and which claims benefit under 35 U.S.C. §119(e) of U.S. Provisional Application No. 61/321,582, filed Apr. 7, 2010, the contents of which are incorporated herein by reference in their entireties.

FIELD OF INVENTION

The present invention relates to processes to recover chemicals from condensates at pulp and paper mills. In particular, the invention relates to a process for recovering natural products such as but not limited to manool and geranyl linalool from kraft mill evaporator condensates.

BACKGROUND OF THE INVENTION

Pulp is produced from raw wood material and is the basic ingredient in the production of paper. The objective of pulping is to separate and recover cellulose fibers from lignin and other wood constituents with maximum yield and minimum fiber degradation. Kraft pulping is the most common process, and accounts for approximately two-thirds of worldwide pulp production.

The kraft pulping process involves treating or 'cooking' wood chips with a mixture of sodium hydroxide (NaOH) and sodium sulfide ($Na_2S$), known as white liquor, to break the bonds that link lignin to cellulose and produce the cellulose fibers used to make paper. Non-fibrous material and spent cooking chemicals are then sent to a recovery process, where the pulping chemicals and energy are recovered via multiple evaporation steps for concentration of pulping waste liquid (black liquor) which is then burned. Large scale evaporators are used in the evaporation steps, and produce condensates which contain substances, some of which have been reported to be toxic when released to the environment (Belknap, A. M., K. R. Solomon, D. L. MacLatchy, M. G. Dubé and L. M. Hewitt. 2006. *Environ. Toxicol. Chem.* 25(9):2322-2333; Hewitt, L. M., S. A. Smyth, M. G. Dubé, C. I. Gilman and D. L. MacLatchy. 2002. *Environ. Toxicol. Chem.* 21:1359-1367; and Hewitt, L. M., T. G. Kovacs, M. G. Dubé, D. L. MacLatchy, P. H. Martel, M. E. McMaster, M. G. Paice, J. L. Parrott, M. R. van den Heuvel, and G. J. Van Der Kraak. 2008. *Environ. Toxicol. Chem.* 27(3):682-697).

Tall oil (also called liquid rosin or tallol) can be collected from the black liquor as a byproduct of the process, and can generate significant revenues when sold for use in products such as adhesives, rubber and emulsifiers. Otherwise, technologies have been developed to remove or reduce remaining pollutants before they are discharged in the mill effluent, for instance by biological treatment to metabolize and consume residual organic material. Apart from tall oil, however, there has been very little attention given to the recovery of natural products of commercial value.

The present invention is therefore directed to recovery methods to extract useful chemicals from pulp and paper waste waters.

SUMMARY OF THE INVENTION

It is an object of the invention to provide methods to extract natural product chemicals, and/or their derivatives, from pulp and paper waste waters.

According to an aspect of the present invention there is provided a process for isolating at least one target compound (including but not limited to manool, geranyl linalool, ethyl guaiacol, eugenol, veratraldehyde, squalene, terpin, cholesterol, beta-sitosterol, campesterol, stigmasterol, stigmastenol and dehydroabietic acid, including all isomeric configurations such as enantiomers and epimers) from pulp and paper waste water, the process comprising the steps of:

obtaining a condensate from a recovery evaporator of a pulp and paper mill, the condensate being substantially free of higher molecular weight (approximately >1000 Da) cellulose and/or lignin and/or lignin-derived material, extracting the condensate by solid phase extraction (SPE), liquid-liquid extraction or solid-liquid extraction to produce an extract containing said at least one target compound, optionally, purifying said at least one target compound from the extract by thermal fractionation (such as distillation, e.g. vacuum distillation, and related processes), chromatographic separation (such as normal and reverse phase or affinity purification), recrystallization or combinations thereof.

In certain embodiments, the process may further comprise steps of filtering or centrifuging the condensate or RO retentate to collect water insoluble material and extracting the insoluble material with the organic solvent. In these and other embodiments it may also be preferable to adjust pH of the condensate or RO retentate to enhance precipitation of the at least one target compound.

In an embodiment, the condensate is from a $1^{st}$, $2^{nd}$, $3^{rd}$, $4^{th}$, $5^{th}$ or higher effect recovery evaporator, more preferably from a $5^{th}$ effect or higher recovery evaporator.

In a further embodiment, the condensate may be a dewatered, concentrated $5^{th}$ effect condensate, for example but not limited to the dewatered, concentrated $5^{th}$ effect condensate that can be obtained from a pulp and paper mill incorporating a reverse osmosis system. In particular, but without wishing to be limiting in any way, the condensate may be derived from a reverse osmosis feed or retentate.

The process described herein may further optionally incorporate a step of adjusting the pH of the condensate, and in an embodiment the pH will be adjusted to less than about pH 13. In a further embodiment, it may be advantageous to adjust the pH of the condensate to from about pH 3.5 to about pH 4.5 or even lower. In certain embodiments, it may be preferable to lower the pH of the condensate to approximately pH 2.

The starting material in the process, or condensates, may be derived from any pulp and paper mill that produces waste waters containing the target compound(s), and most preferably from a stage in the processing in which higher molecular weight (approximately >1000 Da) cellulose and/or lignin and/or lignin-derived material has been mostly, substantially, or entirely removed. In certain embodiments, the pulp and paper mill may be a softwood or hardwood mill. Of interest will be those mills which process softwood, for example but without wishing to be limited to varieties including pine, spruce, fir and combinations thereof. Also of interest are mills which process hardwoods, particularly North American hardwoods, including but not limited to maple, aspen, and birch, or South American hardwoods including but not limited to the *Eucalyptus* genus varieties, as well as combinations thereof.

In the described process, the organic solvent may include but is not limited to dichloromethane (DCM), ethyl acetate, hexane, heptanes, toluene, methyl t-butyl ether (MTBE), ethanol, methanol, isopropanol and combinations thereof. In certain advantageous embodiments the organic solvent comprises ethyl acetate.

In one non-limiting embodiment of the described process, the condensate is filtered and extracted by solid phase extraction (SPE). In this embodiment, the filter can be but is not limited to filter paper or a glass fiber filter. For example, but without wishing to be limiting, filter paper or a glass fiber filter having a pore size of 0.22-8 μm can be used.

The filtered condensate can be extracted using SPE that is eluted with a plurality of solvents, for example but without wishing to be limited to dichloromethane (DCM), methanol, ethyl acetate, toluene, and hexane. In one particular non-limiting embodiment, the filtered condensate is extracted by SPE that is eluted first with DCM, ethyl acetate, toluene, or hexane, and preferably DCM, followed by elution with methanol.

In the above-described process, the insoluble material can also be extracted to increase yields of the target compounds, for example but not limited to extraction methods including solid-liquid extraction such as Soxhlet, shake and sonication techniques. Without wishing to be limiting in any way, the insoluble material can be first extracted with DCM, ethyl acetate, toluene, or hexane, more preferably DCM, followed by extraction with methanol.

The solid phase material of the SPE may be obtained commercially, and may include but is not limited to silica-based bonded phases (including C18 and C8) polymer-based phases such as styrenedivinylbenzene (e.g. Isolute ENV+) and mixed phases (e.g. Oasis HLB). In a preferred embodiment, the solid phase material is a reversed-phase macroporous hyper-crosslinked co-polymer resin, and in one specific but non-limiting embodiment, is Oasis HLB. Without limitation the solid phase may be free resin material or in pre-packed cartridges.

In a further non-limiting embodiment of the described method, the condensate may be extracted by liquid-liquid extraction. In certain embodiments it may be preferable to extract the condensate without filtering, although the filtering step may still be used albeit with reduced yields and/or additional extraction steps. This is primarily because the target compounds have been found to precipitate in the evaporator condensates, depending upon the water content, target compound solubility and target compound concentration.

In the above-described embodiment, yet without wishing to be limiting in any way, the unfiltered condensate can be extracted using a plurality of water immiscible solvents, for example: dichloromethane (DCM), methanol, ethyl acetate, toluene, and hexane. In certain non-limiting embodiments, the unfiltered condensate is extracted first with DCM, ethyl acetate, toluene, or hexane, preferably hexane, followed by extraction with ethyl acetate.

The solvent extraction processes described herein may also be conducted in either batch or continuous modes. The following are examples of illustrative embodiments of batch and continuous extraction modes. However, these are not intended to be limiting in any way.

In a batch process the feed, which can be but is not limited to a condensate or RO retentate, either filtered or unfiltered, or the solid material obtained from the filtering and/or centrifugation step, or an extract of any one thereof, is added to a batch reactor (such as but not limited to mixer-settlers) or column type extractors (such as but not limited to reciprocating, pulsed or rotating columns) optionally equipped with a stirring apparatus or other means for mixing, prior to, subsequent to or together with the desired solvent and, in the case of SPE extraction, solid phase material. The batch is then mixed/agitated and allowed to come to equilibrium. The fluids and any solids in the batch reactor can then be separated, for instance by gravity settling, and the desired phase withdrawn. Single stage extraction can be used in certain embodiments, or more than one stage can be used in which case multiple solvent-washes are applied. It is also envisioned that a countercurrent extraction process may be used. For instance, yet without wishing to be limiting, the feed to each extraction stage can be contacted with solvent from a preceding stage i.e., the feed to the first stage is contacted with the extract from the second stage, and the feed to second stage is contacted with the extract from the third stage, and so forth. This countercurrent contact results in the gradual enrichment of the solute in the solvent phase across the extraction process. Due to the high efficiency, the quantity of solvent required for countercurrent extraction is typically reduced, resulting in a more concentrated extract, and in certain embodiments may be preferred.

For larger volume operation and, in some cases additional efficiency in solvent use, a continuous extraction mode may be selected. In a continuous process the feed can be but is not limited to a condensate or RO retentate, either filtered or unfiltered, or the solid material obtained from the filtering and/or centrifugation step, or an extract of any one thereof. Continuous extractors may include but are not limited to annular centrifugal contactors, and counter-current extractors. In certain preferred yet non-limiting embodiments, a countercurrent continuous flow extractor can be used in which the feed and solvent flow countercurrently.

The extracts obtained by the above-described methods can also be further processed to purify the target compounds. Extracts may first be dried to remove residual water. For example, yet without wishing to be limiting, drying may include treatment with sodium sulfate ($Na_2SO_4$). Without wishing to be limiting, the target compound(s) can be separated in the extracts by thermal fractionation, for example by distillation. Alternately, or in addition, the solvent in the extract can be removed, for example by evaporation, and separation achieved using chromatography, that may include but not be limited to normal phase, reverse phase, affinity phases, or ion exchange methods, to further isolate the target compounds.

Additional purification steps can also be used as desired, and depending upon the required purity of the target compounds.

The present invention also relates to an organic extract comprising at least one target compound (including but not limited to manool, geranyl linalool, ethyl guaiacol, eugenol, veratraldehyde, squalene, terpin, cholesterol, beta-sitosterol, campesterol, stigmasterol, stigmastenol and dehydroabietic acid, including all isomeric configurations such as enantiomers and epimers) enriched or isolated from pulp and paper waste water, the organic extract prepared by a process comprising the steps of: obtaining a condensate from a recovery evaporator of a pulp and paper mill, or a concentrated condensate derived from reverse osmosis treatment, the condensate being substantially free of higher molecular weight (approximately >1000 Da) cellulose and/or lignin and/or lignin-derived material; optionally filtering the condensate to remove insoluble material; and extracting the condensate with an organic solvent by solid phase extraction (SPE) or liquid-liquid extraction to produce the extract containing the target compounds.

In an embodiment, the organic extract can be further processed using purifying steps such as, but not limited to, thermal fractionation (including but not limited to distillation), chromatographic separation, recrystallization, ion exchange, chelation, adsorption/desorption, lyophilization and sublimation or combinations thereof.

The extract can also be provided in a variety of forms, including but not limited to oils and other concentrated liquid forms, or in dried forms such as but not limited to crystals, powders and the like.

The above described organic extract can be subjected to the same extraction and purification steps and derived from the same starting materials as described above and outlined in the detailed description and experiments that follow. In addition, it is to be understood that purified target compounds and other extractives obtained from the above extracts and produced by the above process are similarly provided herein.

BRIEF DESCRIPTION OF THE DRAWINGS

These and other features of the invention will become more apparent from the following description in which reference is made to the following figures:

(FIG. 12A) RO retentate (ambient was pH 13); (FIG. 12B) condensate (ambient was pH 12). * denotes incomplete mixing of retentate, where manool associated with surface oils is not accounted for.

FIG. 13A depicts green chromatogram profiles material extracted using ethyl acetate in a continuous liquid/liquid apparatus from condensate adjusted to pH 2. FIG. 13B depicts orange chromatogram profiles material recovered from solid phase extraction of the residual condensate following ethyl acetate extraction. Both chromatograms were adjusted to the same vertical scale accounting for dilutions made during processing.

DETAILED DESCRIPTION

Figure 1:
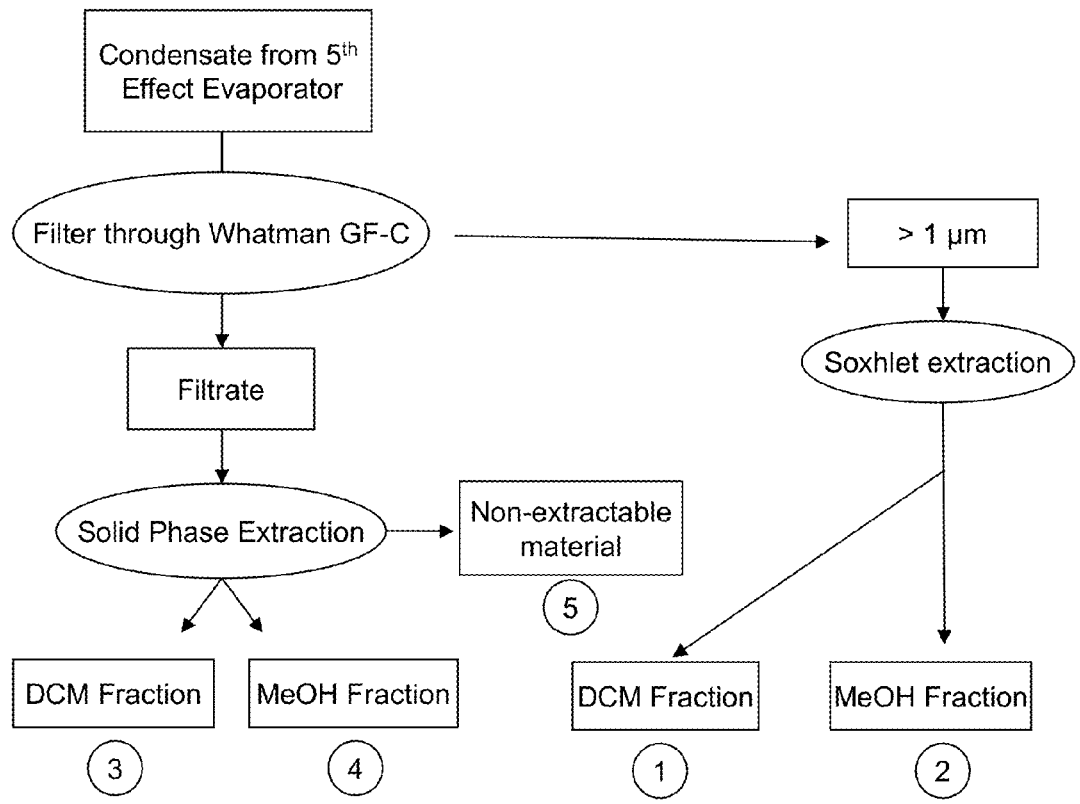
FIG. 1 is a flow diagram illustrating the fractionation method of Example 1.

The inventors have found that valuable natural product compounds can be obtained from kraft mill recovery condensates, including but not limited to manool (CAS#000596-85-0) and geranyl linalool (CAS#001113-21-9).

Manool is valued because it can be converted into compounds useful, for instance, in the perfumery and flavoring industries. It is a terpenoid having the following structure:

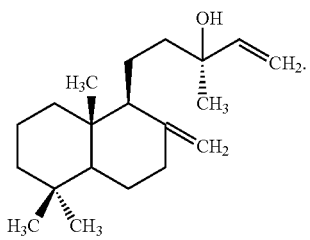

Synthetic processes for production of manool have been described, for instance, in U.S. Pat. No. 7,294,492 which describes a method for preparing manool from larixol by microbiological processing. However, manool is more commonly extracted from different plant types, including *Salvia sclarea* (clary sage) (Popa, D. P. and Salei, L. A. 1974, Manool from *Salvia sclarea*, *Chemistry of Natural Com-* pounds, 10:3, 409), or New Zealand pink pine (*Halocarpus biformis*) (McDonald, I.R.C, 1964, Manool from *Dacrydium biforme*, *Chemy Indust, NZ*, 1:1, 16-17; and Merz, D. F and Ritchie, W. J, 1970, The production of crystalline manool from *Dacrydium biforme*, *NZ Journal of Science*, 13:2, 268). However, difficulties with yields, slow production turnaround, impurities and availability of source material have limited the availability of this compound.

Geranyl linalool is a fragrance ingredient used in cosmetics, fragrances, soaps and other toiletries, as well as in household cleaners and detergents (Lapczynski A et al, 2008, Fragrance Material Review on Geranyl Linalool, *Food and Chemical Toxicology*, 46, S176-S178) with the following structure:

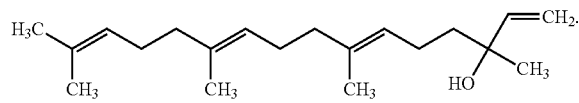 [SMILES: C=CC(C)(O)CC/C=C(\C)CC/C=C(\C)CCC=C(C)C]

A process for preparing the compound is described in: Odinkov, V. N., Akhmetova, V. R., Savchenko, R. G., Mallyabaeva, M I., and Lobanova, N.Y. 1998. Ozonolysis of alkenes and study of reactions of polyfunctional compounds. LIX. New approach to synthesis of isophytol and (E,E)-geranyllinalool, isoprenoid synthons for the alpha-tocopherol and (E,E)-alpha-tocotrienol. *Russ. J. Org. Chem.* 34:1099-1101.

Most methods and references that refer to extracts containing natural products such as these are produced through the extraction of the raw product, such as extraction of leaves, bark, saw dust, wood chips, etc. In using waste water from the pulping process, and evaporator condensates in particular, a large part of the extraction, or separation of compounds of interest from cellulose and/or lignin has already been performed, and solid material (such as wood) does not have to be handled. The absence of these materials in recovery evaporator condensates provides an advantage over other industrial processes, where natural products are isolated from plant material and high molecular weight interferences must be removed during purification.

The method is particularly useful for recovering these chemicals from a reverse osmosis (RO) retentate, such as that obtained using the process described in U.S. Pat. No. 6,110,376 for reducing condensate BOD and toxicity. During RO treatment, not only are condensate chemicals not destroyed or altered, they are conveniently concentrated for subsequent recovery, thus reducing the time, cost and/or effort in isolating substances of commercial value. Moreover, the RO feed and retentate do not contain appreciable amounts of higher molecular weight (approximately >1000 Da) cellulose and/or lignin and/or lignin-degradation products.

Without wishing to be limiting, the starting material for the chemical extraction can be taken from a $1^{st}$, $2^{nd}$, $3^{rd}$, $4^{th}$, $5^{th}$ or a higher effect recovery evaporator at a conventional kraft pulp and paper mill or from condensates at other types of pulp and paper mills. In a preferred embodiment, the starting material is taken from a $5^{th}$ effect condensate, and optionally from a pulp and paper mill that incorporates a reverse osmosis system. In another non-limiting embodiment, the starting material can be taken from a RO-retentate, or a dewatered concentrated $5^{th}$ effect condensate. The use of $5^{th}$ effect condensates and derivatives thereof, such as a RO-retentate or other dewatered concentrated $5^{th}$ effect condensate, is particularly advantageous due to the high concentration of volatile and semi-volatile compounds without the presence of higher molecular weight (approximately >1000 Da) cellulose and/or lignin, and/or lignin-derived material.

In addition, since the pulping process is a harsh environment with high cooking temperatures (130-180° C.), very high pH's (pH>13) and very high salt content, and the black liquor evaporation process is carried out at high temperature, high vacuum and high pressure, any chemical that remains in the $5^{th}$ effect condensate or derivative thereof must be very chemically stable (e.g. not oxidisible, etc). Thus, more severe extraction conditions can be used in the extraction and purification process, such as high or low pH's, temperatures and pressures to obtain the end products.

EXAMPLES

Example 1

Solid Phase Extraction

Black liquor condensates were collected from Canadian kraft mill chemical recovery evaporators from a pulp and paper mill processing softwood (spruce, pine, fir) tree species. The condensates were sampled specifically from the $5^{th}$ effect evaporator (or final black liquor evaporator prior to discharge) in stainless steel containers and shipped to the laboratory for purification using the bench scale method described below, and outlined in the flow diagram in FIG. 1.

Figure 2:
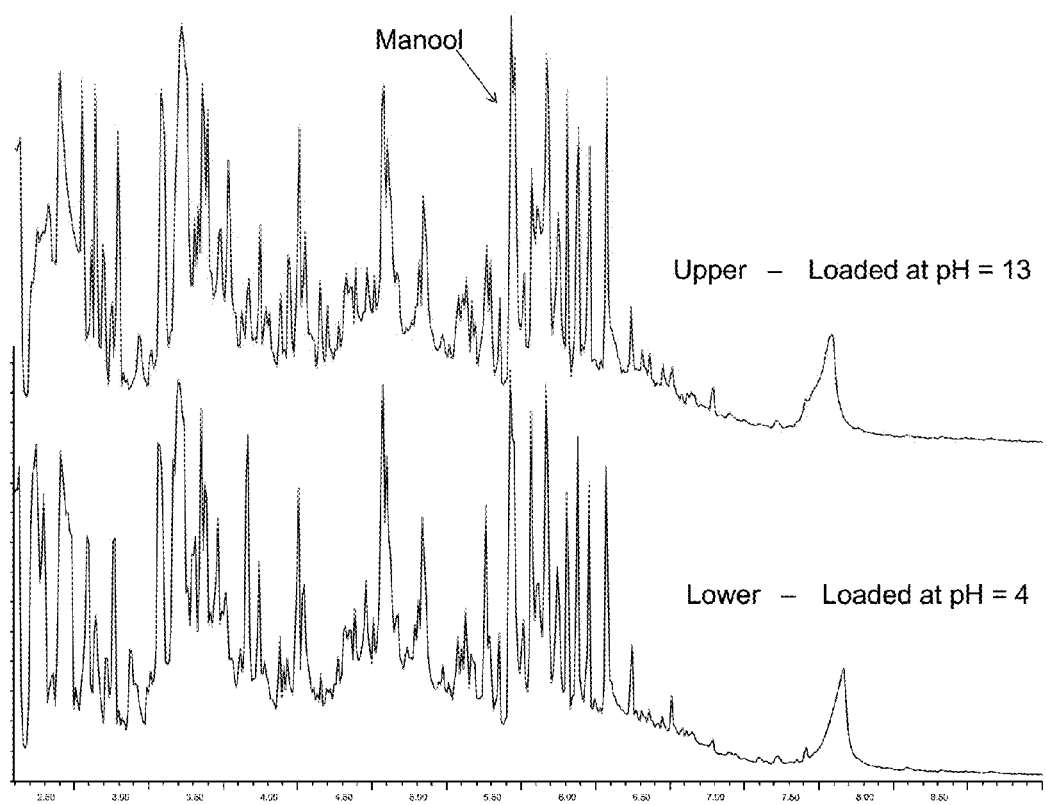
FIG. 2 shows chromatographs of filtered 5$^{th}$ effect condensate loaded onto a Oasis HLB SPE cartridge at pH 4 and at pH 13. Shown is the DCM eluted extract.

Upon arrival, condensate pH (typically >10.5) was lowered using high purity inorganic acid (i.e. hydrochloric acid) to pH=4.0±0.5. It should be noted, however, that subsequent steps of solid phase extraction (SPE) and filtering at ambient pH (pH=10.5) has also been successfully carried out. In the case of manool, geranyl linalool and other terpenes, they are essentially considered "neutrals" so they are extracted regardless of pH. FIG. 2 shows chromatographs from a condensate sample that was loaded onto the SPE cartridge at two pH's: pH=10.5 and pH=4.

pH-adjusted condensate was then filtered through 1.2 µm glass fibre filter paper (i.e. Whatman GF-C). Fouled filter papers were combined, air dried, cut into 1 cm squares and then solvent extracted using a Soxhlet apparatus for a minimum of 12 h. All solvents used throughout are distilled in glass (DIG) grade. Two solvents were used sequentially (12 h each) in the filter paper extractions to produce two fractions: first using dichloromethane (FP-DCM), and second using methanol (FP-MeOH). Soxhlet conditions and solvent selections (that also included ethyl acetate and hexane) were optimized for recovery of condensate extractives (phenolics and diterpenes). It should be noted that while DCM and MeOH were the optimized solvents in this experiment, ethyl acetate, toluene, and hexane can also be used. Condensates were then subjected to solid phase extraction (SPE).

Figure 3:
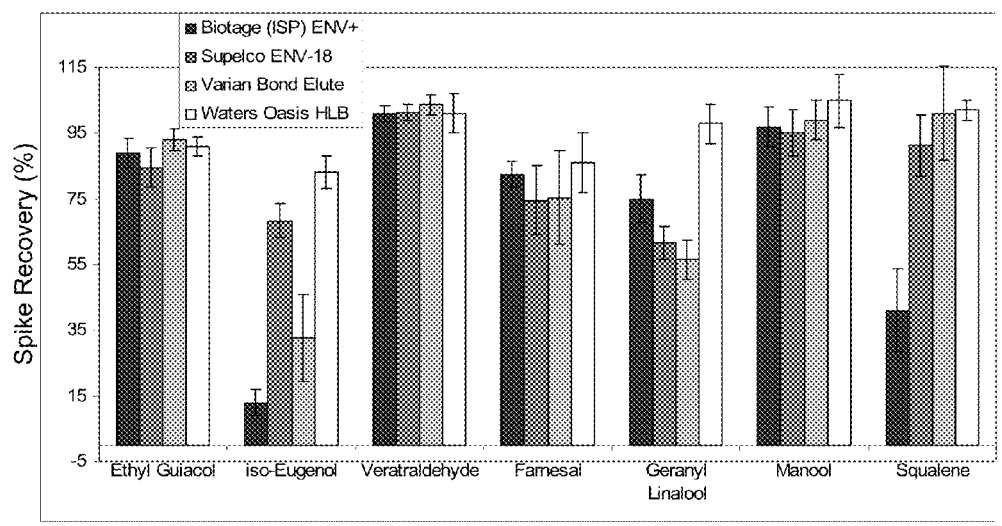
FIG. 3 shows a graph illustrating relative spike and recovery of compounds using four Solid Phase Cartridges (ENV+, ENV-18, Bond Elut, Oasis HLB). 1 mL of standard solution (1 mg/mL) was diluted into 250 mL of water (pH=4) and loaded onto cartridges (500 mg resin in 6 mL cartridges) with two fractions being sequentially eluted, the first using 10 mL ethyl acetate, and the second using 10 mL methanol. The graph shows comparisons in the relative recoveries from the EtAc (ethyl acetate) fraction. The eluted MeOH (methanol) fraction did not reveal any measurable concentrations of any of the compounds. This graph shows that the Oasis HLB cartridge gives the greatest recovery for all of the compounds, and that recovery of all the compounds is possible from each of the tested SPE cartridges.
Figure 4:
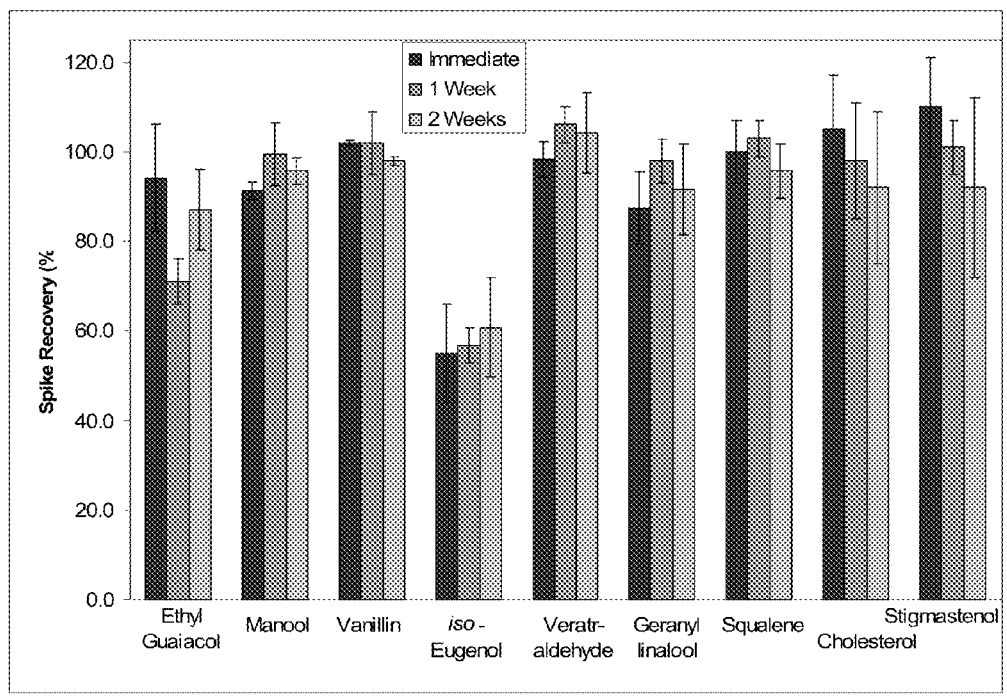
FIG. 4 shows a graph illustrating relative recoveries of compounds from Oasis HLB SPE cartridges following three different time periods: Immediate, after 1 week and after 2 weeks. 1 mL of standard solution (1 mg/mL) was diluted into 250 mL of water (pH=4) and loaded onto cartridges (500 mg resin in 6 mL cartridges). Two fractions were eluted sequentially using 40 mL each of DCM and MeOH. As in FIG. 3, the MeOH fraction did not contain detectable amounts of any of the compounds. No difference in recovery of compounds was noted over a two-week period, and increased recovery of most compounds (and all terpenoids) was observed using DCM as the initial eluting solvent.

The pH adjusted condensate filtrate was fortified with 2% (v/v) methanol followed by SPE extraction as follows:
i. Condensates were extracted at an optimized ratio of 1 g solid phase/0.1 L.
ii. Solid phase selection was made from comparative studies of commercially available solid phases that included C18, C8, Isolute ENV+ (styrenedivinylbenzene), ENVI-ChromeP, Bond Elut (Varian) and Oasis HLB (Waters Corporation). Oasis HLB, a reversed-phase macroporous hyper-crosslinked co-polymer resin, was selected as the optimal solid phase for recovery of phenolics and diterpenes (see FIGS. 3 and 4).
iii. Prior to extraction, each SPE cartridge was equilibrated with the following solvents (10 mL each): DCM, Methanol, HPLC Grade water (adjusted to pH=4).

iv. Methanol fortified condensate was processed through each SPE cartridge at a rate of 1-2 drops per second using a slight vacuum (~15 mm Hg).
v. Following the complete extraction of the sample, the resin was washed by eluting 10 mL/g resin of HPLC grade water pH adjusted to 4.0 to remove residual salts.
vi. The "loaded" SPE cartridges were then completely dried using a drying time at full vacuum for 1 h/g solid phase.
vii. The loaded cartridges were then eluted sequentially using 40 mL solvent/g solid phase to produce two fractions: firstly, using DCM (SPE-DCM), secondly using methanol (SPE-MeOH). It should be noted, however, that these solvents, their order and volumes were optimized from comparative studies using hexane, methyl t-butyl ether (MTBE), ethyl acetate, toluene, methanol and DCM. The optimal solvents were DCM and MeOH, although other solvents in various eluting orders have also been trialled, including hexane, MTBE, ethyl acetate, and MeOH as first eluting solvent. DCM was chosen as first eluting solvent as it eluted the most material using the smallest solvent volume.
viii. The filter paper and SPE solvent fractions were dried using an excess amount of anhydrous sodium sulfate via gravity filtration.
ix. All 4 fractions were concentrated using a gentle stream of nitrogen, or rotary evaporation. Depending on end usage, samples can be either concentrated or evaporated to dryness and reconstituted in different solvents.

Figure 5:
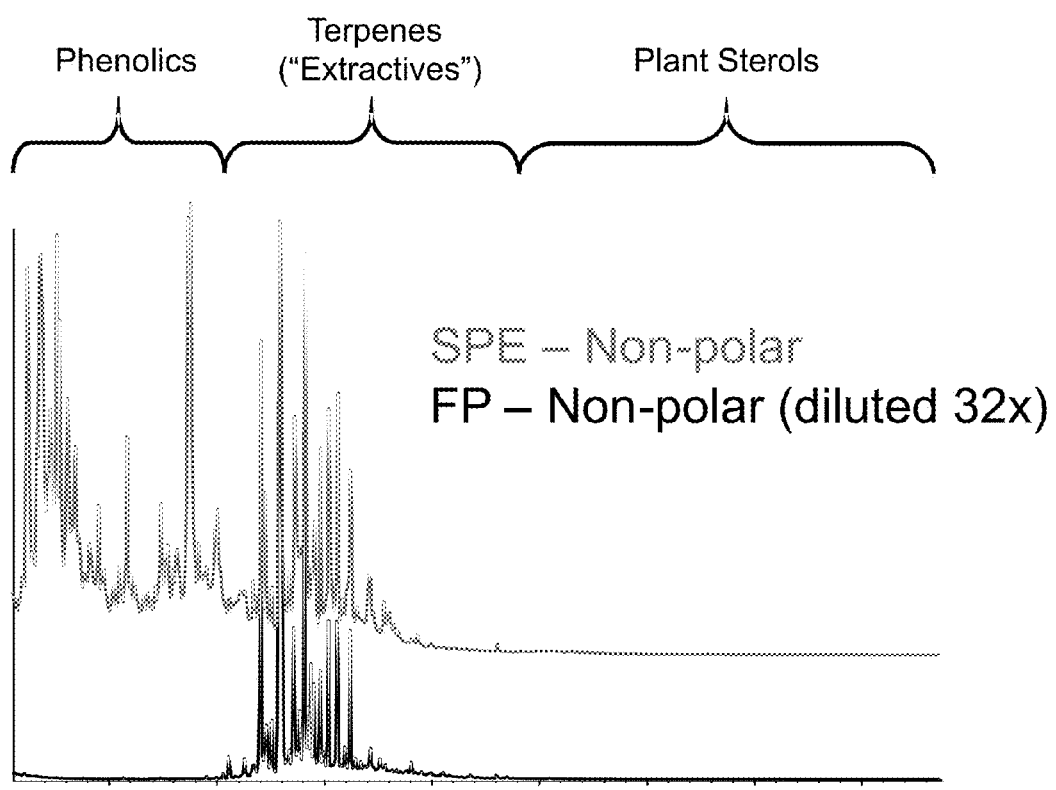
FIG. 5 shows GC-MS (gas chromatography-mass spectrometry) chromatographs of SPE and filter paper (FP) non-polar fractions (DCM fractions).
Figure 6:
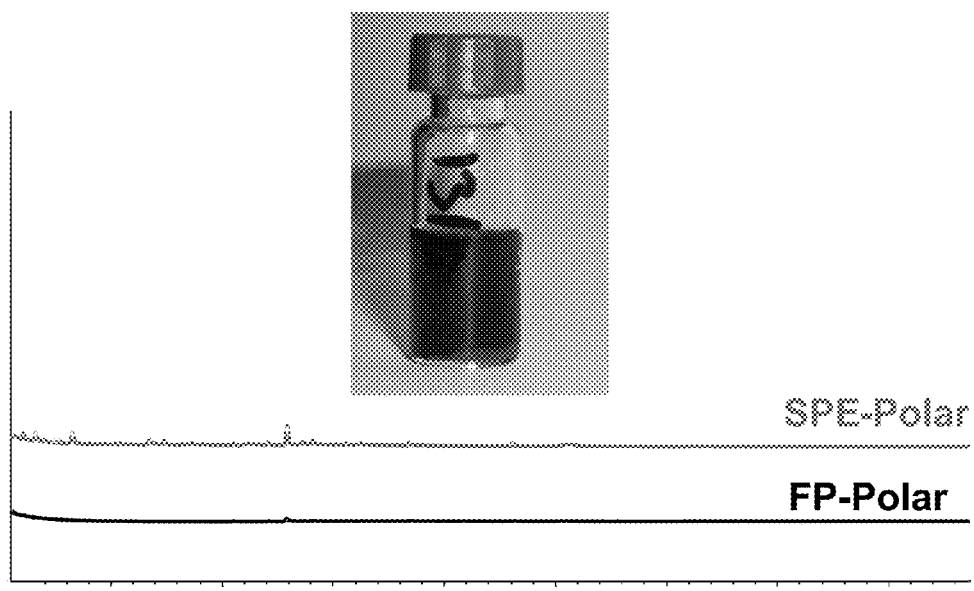
FIG. 6 shows GC-MS Chromatographs of SPE and FP polar fractions (methanol fractions).

Using this protocol, a total of five fractions were produced, including (i) FP-DCM: solid material extracted off the filter paper using dichloromethane, and comprising medium polarity to non-polar compounds; (ii) FP-MeOH: solid material extracted off the filter paper using methanol, and comprising polar compounds; (iii) SPE-DCM: SPE extracted material eluted using dichloromethane, and comprising non-polar compounds; (iv) SPE-MeOH: SPE extracted material eluted using methanol, and comprising polar compounds; and (v) non-extractable residual condensate not retained by the SPE cartridge, which comprises highly polar compounds. The specific compounds identified in these fractions are listed in Table 1, together with relative recoveries and a comparison with the recoveries obtained in Comparative Example 1 (experimental follows below). The GC chromatographs of the fractions can be seen in FIGS. 5 and 6.

In the above method there was no carryover of extractable compounds between methods of extractable material (i.e. DCM followed by MeOH), such that chemically-distinct extracts were produced. In addition, filtering removed the bulk of the targeted compounds, particularly manool and geranyl linalool. Further, the use of HLB SPE cartridges allowed for the use of DCM as an eluting solvent, which elutes all of the target compounds in one fraction. Ethyl acetate, methanol (as first solvent), and hexane also elute the target compounds, but with reduced elution efficiency. Finally, it was noted that the FP-MeOH and SPE-MeOH fractions did not contain any compounds that were detectable using conventional GC-MS. The fact that any compounds in this fraction were not eluted using the first solvent (in this case, DCM) indicates that these are very polar compounds. Different analytical techniques are therefore required for analyzing this fraction and to identify whether any commercially useful compounds are present in these particular fractions.

Example 2

Liquid-Liquid Extraction

Figure 7:
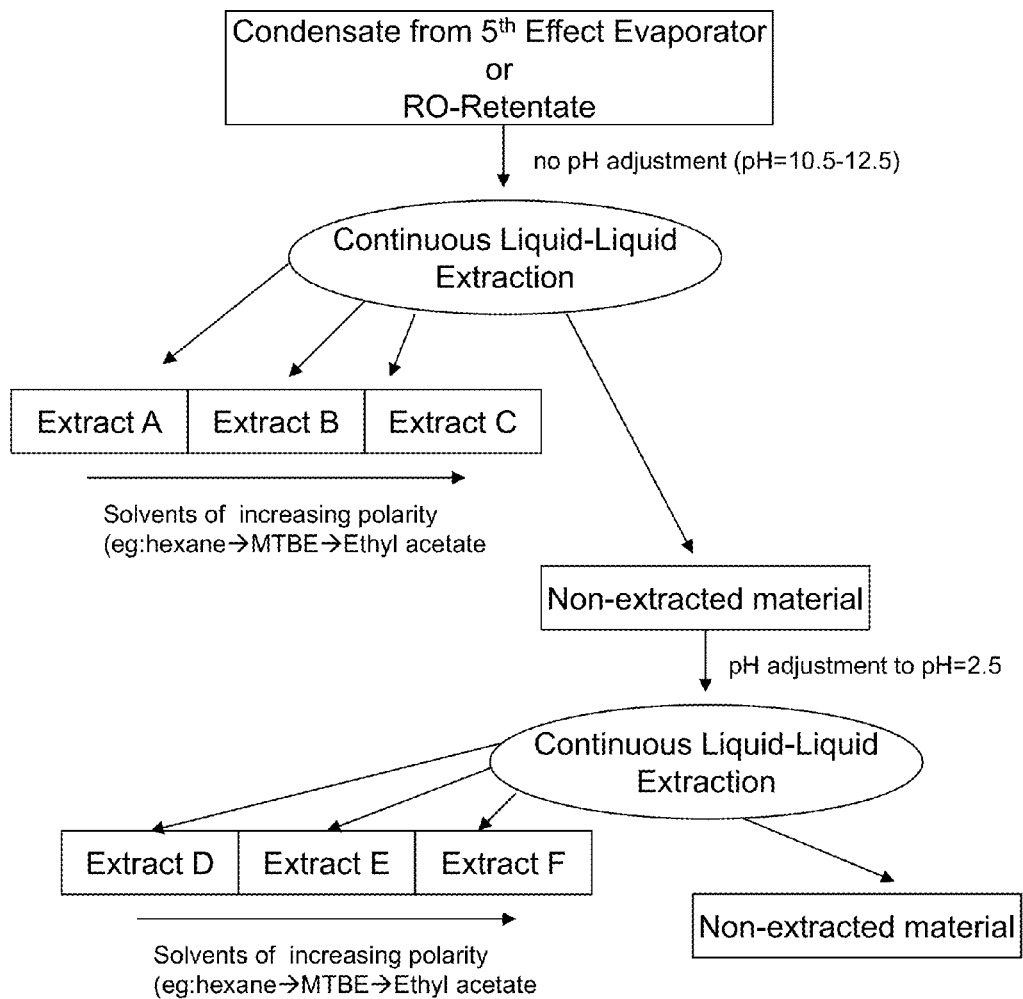
FIG. 7 is a flow diagram illustrating the fractionation method of Example 2.

Samples from a Canadian kraft pulp and paper mill were obtained and initially treated identically to Example 1, although unlike Example 1 the samples were not filtered prior to extraction. The general method is outlined in the flow diagram in FIG. 7.

A 500 mL volume of sample was poured into a continuous liquid-liquid extractor, and 500 mL of water immiscible solvent was poured into the associated round-bottomed flask. The solvent was heated and continually maintained under reflux, allowing it to pass through the condensate sample and extract material before cycling back to the round bottom flask. Following a minimum of 12 hours of cycling, the round bottom flask was removed. Both extraction solvent and the extracted material were contained in the round bottom flask. The target compounds extracted from the condensate and now contained in the solvent were then dried using anhydrous sodium sulfate, and the solvent was evaporated off using a rotary evaporator thus producing an oily extract. This extract can then be treated in the same manner as the SPE and FP extracts to further fractionate, isolate and purify target compounds including manool, geranyl linalool and other target extractives, for instance but not limited to using HPLC methods.

TABLE 1

Measured concentrations of FP-DCM and SPE-DCM fractions from samples obtained in two trials. FP-MeOH and SPE-MeOH are not shown as none of these specific compounds were detected using GC-MS.

|  | Comp. Ex. 1 | 1st batch May 2009 | | | | | | 2nd batch July 2009 | | | | | |
|---|---|---|---|---|---|---|---|---|---|---|---|---|---|
|  | Recov. | SPE | | Filter Paper | | Total | | SPE | | Filter Paper | | Total | |
|  | mg/L | mg/L | kg/d | mg/L | kg/d | mg/L | kg/d | mg/L[a] | kg/d[b] | mg/L | kg/d | mg/L | kg/d |
| Ethyl Guaiacol | 1.228 | 2.18 | 9.42 | nd | nd | 2.18 | 9.42 | 3.59 | 15.52 | nd[c] | nd | 3.59 | 15.52 |
| Manool | 0.611 | 1.16 | 5.03 | 40.66 | 175.65 | 41.82 | 180.68 | 2.01 | 8.69 | 47.14 | 203.63 | 49.15 | 212.32 |
| Iso-eugenol | 0.131 | 4.36 | 18.85 | nd | nd | 4.36 | 18.85 | 1.18 | 5.11 | nd | nd | 1.18 | 5.11 |
| Veratraldehyde | 0.06 | nd | nd | nd | nd | nd | nd | 0.03 | 0.14 | nd | nd | 0.03 | 0.14 |
| Geranyl linalool | 0.138 | 0.26 | 1.11 | 5.64 | 24.38 | 5.90 | 25.49 | 0.35 | 1.52 | 8.61 | 37.21 | 8.97 | 38.73 |
| Squalene | na[d] | nd | nd | 0.16 | 0.69 | 0.16 | 0.69 | 0.02 | 0.11 | 0.25 | 1.10 | 0.28 | 1.21 |

[a]Measured concentration of extracted compound in mg/L (or ppm)
[b]Potential mass of recovered compounds based on 3000 L/min of condensates generated during black liquor recovery process
[c]nd = not detected (but analyzed for)
[d]na = not analyzed The extraction solvents, solvent order and pH trialed in this study include the following:

ethyl acetate, pH=12.5→ethyl acetate, pH=2.5;
DCM, pH=12.5→DCM, pH=2.5→ethyl acetate, pH=2.5;
Hexane→Toluene→DCM→Ethyl acetate (all extracted at pH=12.5, followed by reducing pH to 2.5 and repeating solvent extraction order); and
Hexane→MTBE→Ethyl acetate (first at pH=12.5, followed by pH=2.5).

The condensates and RO-retentate samples both contained solids. In this study it was found that these solids are all extractable, and following liquid-liquid extraction a clear, almost colourless water remains. This is due to very high concentration of the very hydrophobic compounds that precipitate under aqueous conditions. One of the major advantages of this method is that this removes the requirement of filtering the condensate/RO retentate. In fact, the very high solids content of the RO retentate makes filtering difficult due to very quick fouling of the filter paper.

The advantages of this liquid-liquid extraction method over the SPE method of Example 1 are: (i) that there are fewer steps to produce the extract thus resulting in time and cost savings, (ii) cost savings in not requiring SPE materials, (iii) the potential scalability through chemical apparatus and solvent recycling, and (iv) the potential for a continuous industrial method whereas SPE methods would be "batch".

Example 3

Extract Purification

The following method is an example of how the extracts obtained in Examples 1 and 2 can be further purified. The following method is described with reference to the noted samples obtained in the SPE method of Example 1, although the same methodology is applicable to the extracts obtained in the liquid-liquid extraction method of Example 2.

Compounds contained within the FP-DCM and the SPE-DCM fractions were purified using high-pressure liquid chromatography (HPLC) to obtain isolates of individual compounds. The procedure is as follows:

i. Aliquots of each fraction are injected on a normal phase silica column (Phenomenex Luna 250 mm×4.6 mm; 5 μm particle size, 100 Å pore size) at a flow rate of 0.5 mL/min with an optimized elution gradient as follows:
initial conditions of 50:50 hexane/DCM is held for 15 min,
linear ramp to 100% DCM over 10 min, hold for 25 min,
linear ramp to 50:50 dichloromethane/iso-propyl alcohol over 10 min, hold for 10 min.
ii. Fractions containing purified compounds were collected using an automated fraction collector that had been programmed on an elution time window basis.

Purified compounds within HPLC fractions were assessed for purity and quantified for yield calculations using gas chromatography-mass spectrometry (GC-MS) as follows:

i. Fractions were first reduced under a gentle stream of nitrogen to just dryness and then reconstituted in toluene.
ii. Aliquots of each fraction (1 μL) were injected into a GC-MS single quadrupole system (HP 6890, HP 5972 MSD) on a Restek RTX-5 (30 m, 0.25 mm ID, 0.25 μm film thickness) using a He carrier gas.
iii. GC oven temperatures were programmed as follows: 90° C. for 30 s; 40° C./min to 300° C.; hold for 10 min.

Injector temperature 270° C. in splitless mode. The MS ion source temperature was 230° C. operating in electron impact (EI) mode.

iv. Purities of each compound were obtained by full scan GC-MS analysis (m/z 50-500) operating at unit resolution.

Each compound was quantitated for yield by comparing integrated peak areas to those from individual calibrations (6-point) of commercially available authentic standards.

Figure 8:
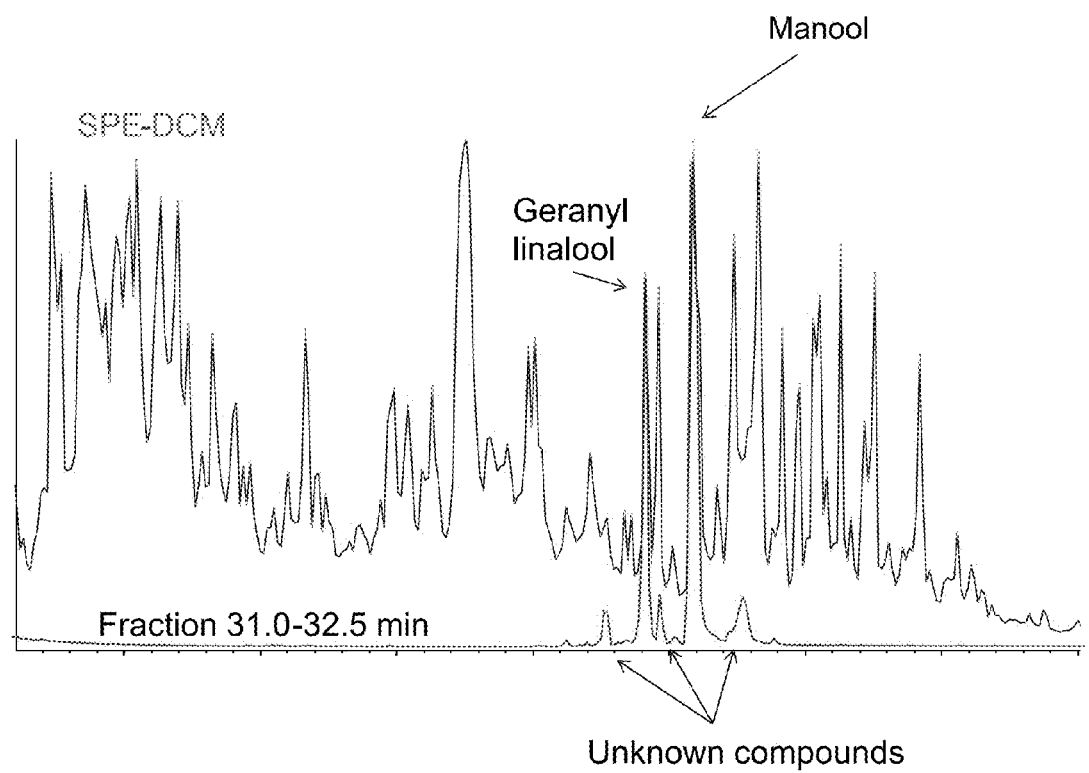
FIG. 8 shows a GC-MS chromatograph of SPE-DCM and the fraction collected using HPLC (high pressure liquid chromatography) fractionation (31.0-32.5 min).

Following GC-MS analysis, the compounds and their respective purities were determined as shown in Table 2. FIG. 8 provides an example of the fraction collected from 31-32.5 min, which contains both geranyl linalool and manool.

TABLE 2

Compounds and Their Respective Purities Following GC-MS Analysis.

| HPLC Fraction Number | HPLC Fraction collection time (min) | Compound (CAS#) | HPLC Fraction Purity (%) |
|---|---|---|---|
| 1 | 3.0-4.5 | Squalene (111-02-4) | 4.4 |
| 2 | 10.0-11.8 | Dehydroabietal (13601-88-2) | 26 |
| 3 | 19.0-23.5 | Ethyl guaiacol (002785-89-9) | 47 |
| 3 | 19.0-23.5 | Isoeugenol isomers (000097-54-1) | 43 |
| 4 | 31.0-32.5 | Manool (000596-85-0) | 60 |
| 4 | 31.0-32.5 | Geranyl linalool (001113-21-9) | 26 |
| 5 | 63.5-66.0 | Terpin (565-50-4) | <0.1 |

Comparative Example 1

Solid Phase Extraction

Before SPE, condensates were filtered (GF/B glass microfiber, 150 mm, 1.0-μm particle retention; Whatman International, Maidstone, UK), fortified with methanol (2% v/v), and pH was adjusted to approximately 4 with 3.0 M hydrochloric acid. Two different cartridges are utilized in series in this protocol, with a styrene divinylbenzene cartridge (ENV, 1 g/6 ml; Isolute Technologies, Mid Glamorgan, UK), followed by a custom graphitized carbon cartridge (Supelclean ENVI-CARB, 80/100 mesh, 500 mg, 2-ml reversible tubes; Supelco, Bellefonte, Pa., USA). Styrene divinylbenzene ENV (SPE-1) cartridges were preconditioned with two cartridge volumes (~12 ml) each of ethyl acetate, methanol, and HPLC-grade water. A total of 250 ml of condensate was processed under vacuum per SPE-1 cartridge, and extracted condensates were collected in filter flasks.

Figure 9:
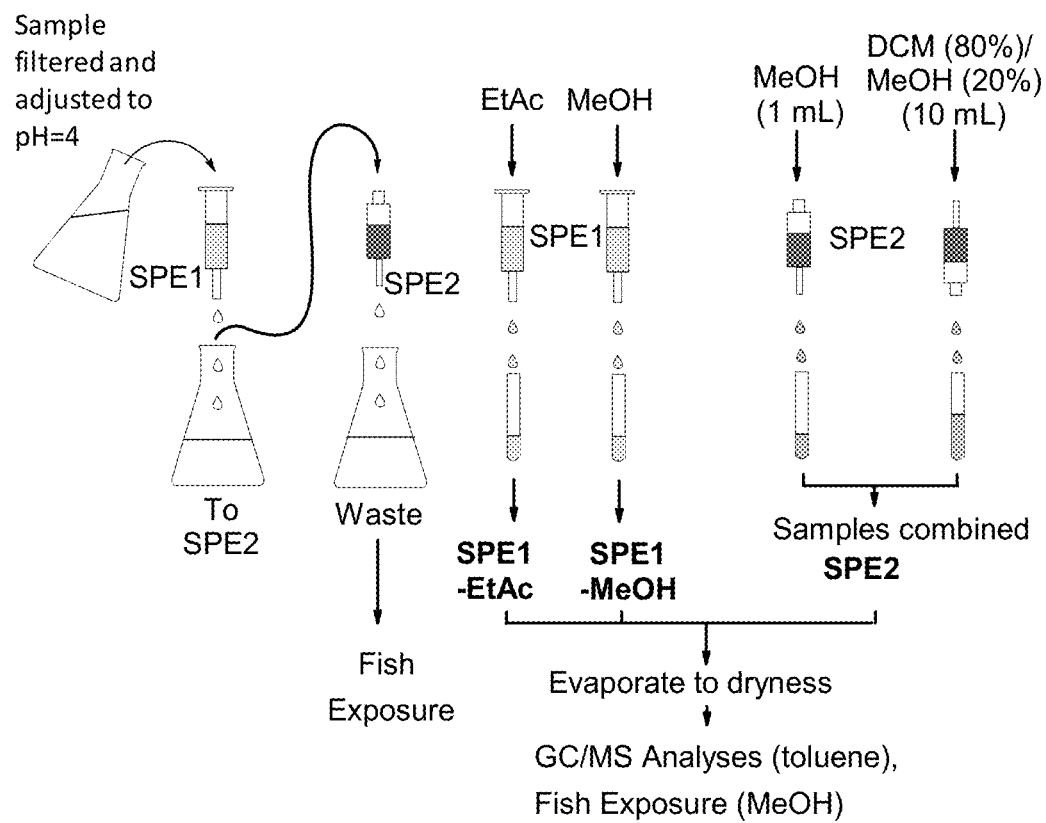
FIG. 9 is a flow diagram illustrating the fractionation method of Comparative Example 1.

Following processing, extractives were eluted into two separate extracts from SPE-1 with two cartridge volumes (~12 ml) of ethyl acetate (SPE-1 EA), followed by two cartridge volumes of methanol (SPE-1 M) per cartridge. The ENVI-CARB (SPE-2) cartridge was preconditioned with 10 ml of 20% (v/v) methanol in dichloromethane, 4 ml of methanol, and 10 ml of HPLC-grade water. Condensates extracted by the SPE-1 cartridge were then processed through the SPE-2 cartridge in the forward direction under vacuum. The SPE-2 cartridge was then eluted with 1 ml of methanol in the forward direction, followed by 10 ml of 20% (v/v) methanol in dichloromethane in the reverse direction. Eluates from the forward and reverse directions were combined to make the SPE-2 eluate. The SPE-1 EA, SPE-1 M, and SPE-2 eluates were evaporated to just-dryness under a gentle stream of ultrapure nitrogen gas ($N_2$; BOC Canada, Mississauga, ON, Canada) with mild heating (30-35° C.) and then reconstituted with toluene to a final condensate equivalent of 1 L/m1 for GC-MS analysis (see flow diagram in FIG. 9).

Reverse-phase HPLC using a water-acetonitrile gradient was also used to fractionate SPE-2 into seven fractions. None of which showed recovery of any compounds using GC-MS. This was later found to be due to evaporation of compounds during workup, and thus the compounds in this fraction were more volatile than water. Further fractionation of SPE2 was unsuccessful due to irreversible binding and inability to further fractionate based on polarity.

Figure 10:
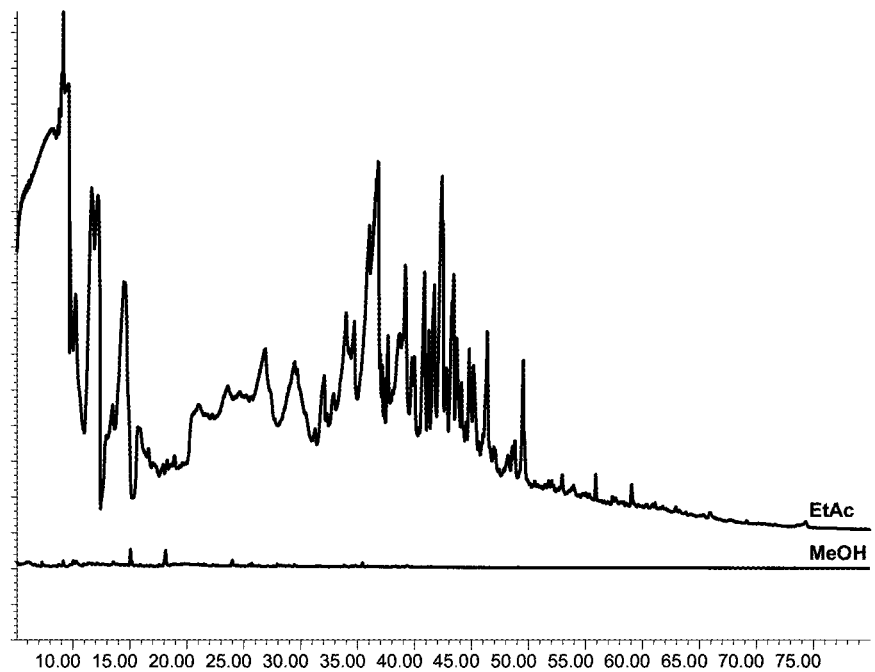
FIG. 10 shows a GC-MS chromatograph of the fractions obtained from SPE1 in Comparative Example 1. Solvent elution order: Ethyl acetate (EtAc)-Methanol (MeOH).
Figure 11:
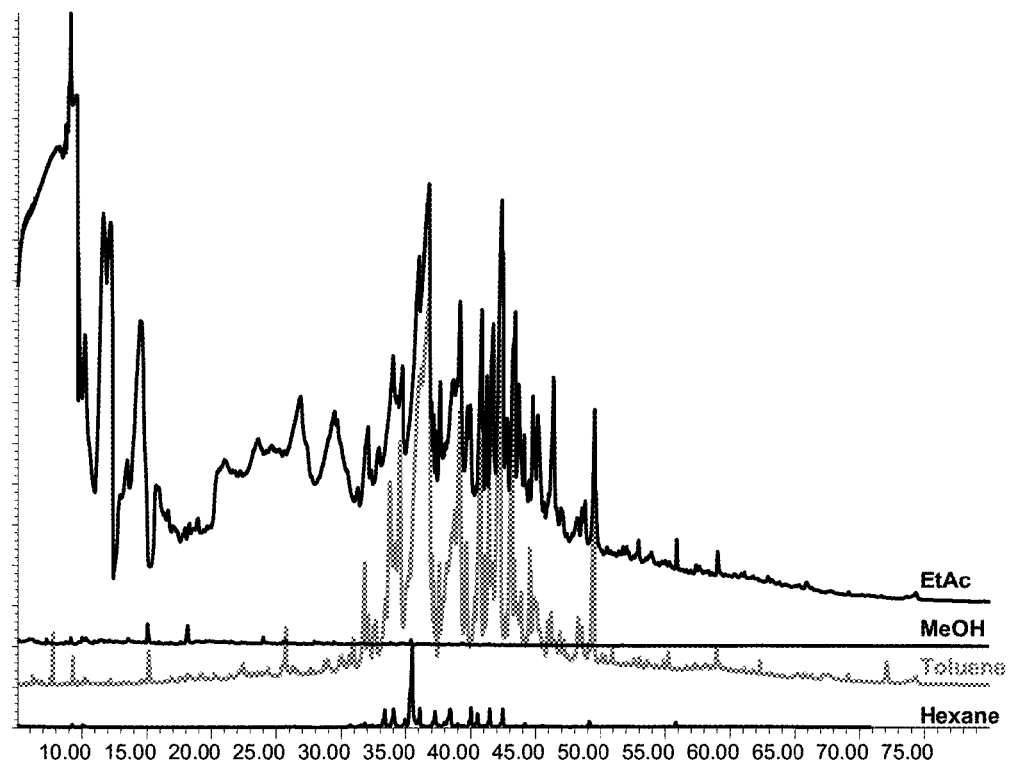
FIG. 11 shows a GC-MS chromatograph of the fractions obtained from SPE1 in Comparative Example 1, followed by additional non-polar solvents. Solvent elution order: Ethyl acetate (EtAc)-Methanol (MeOH)-Toluene-Hexane.

Using this method, the two solvents used to elute SPE1 were insufficient to remove all material from the SPE cartridge. This was seen by using more non-polar solvents (toluene, then hexane) to elute further uneluted material remaining on the column (FIGS. 10 and 11). Compound recoveries using this method are listed in Table 1.

Example 4

Evaluation of Extraction Techniques

To optimize the materials and methods for scale-up, the filtration/SPE extraction method described in Example 1 was compared to treatment by i) centrifugation/solid-liquid extraction and ii) liquid-liquid extraction techniques.

Samples of 5th effect condensates and the RO retentate (dewatered) product stream from a Canadian kraft pulp and paper mill were obtained and initially treated identically to Example 1, although unlike Example 1 the samples were not initially filtered when treated either by centrifugation/solid-liquid extraction or liquid-liquid extraction.
Filtration Followed by Solid Phase Extraction:

Condensates and RO retentates were filtered followed by solid phase extraction at bench scale. Recovery yields were determined, and the results are shown in Table 3.

TABLE 3

Relative yield for Filtration, followed by Solid Phase Extraction of $5^{th}$ Effect condensates and RO retentate derived from condensates.

| Feedstock type | Stream sampled | Extraction method | Manool Recovery (%) |
|---|---|---|---|
| Softwood | Condensate | Filter Paper | 97.5 |
|  |  | SPE | 2.5 |
|  | RO Retentate | Filter Paper | 99.9 |
|  |  | SPE | 0.1 |
| Hardwood | Condensate | Filter Paper | 68.9 |
|  |  | SPE | 31.1 |
|  | RO Retentate | Filter Paper | 98.7 |
|  |  | SPE | 1.3 |

Centrifugation/Solid-Liquid Extraction:
(i) Batch:

Condensates and RO retentates were batch centrifuged followed by solid phase extraction at bench scale. Recovery yields were determined, and the results are shown in Table 5.

Prior to centrifuging it was noted that flocculation occurs in both condensates and RO retentate following pH reductions. With further study it was found that pH 2 provided the greatest observable flocculation (all solids were observed to settle overnight). The target compounds, including manool and other compounds described here, appear to adsorb to any solids present. Accordingly this phenomenon was used to further optimize the recovery of target compounds with detection by GC-MS.

In addition, manool recovery was tested via centrifugation of solids with optimization of centrifugation time, speed and temperature for solids recovery. Trials were carried out at 2,500, 5000, 10,000 and 30,000 rpm; 10, 20, 60 min; 4° C. and 18° C. It was determined that 30,000 rpm at 4° C. for 60 min provided complete settling of solids and visible colloids. These parameters were used to measure mass of solids/oil recovered hardwood, softwood retentate and condensates.

TABLE 4

Solids recovered at pH = 2 from condensates and RO retentate. Total suspended solids (TSS; standard method: 50 mL filtered through 45 mm Whatman GF-C, and dried in desiccator overnight). Centrifuged solids, 20 mL at 30,000 rpm for 60 minutes, bottles dried.

|  |  | TSS mg/L | Centrifuged Solids mg/L |
|---|---|---|---|
| Softwood | Retentate | 5.916 (±0.806) | 6.857 (±0.542) |
|  | Condensate | 0.190 (±0.003) | 0.210 (±0.078) |
| Hardwood | Retentate | 1.498 (±0.003) | 1.750 (±0.014) |
|  | Condensate | 0.028 (±0.006) | 0.030 (±0.006) |

Lower values for TSS reflect the use of filter paper with a pore size of approximately 1.2 μm, meaning that some of the smaller solids will pass through the filter paper.
(ii) Pilot Scale, Continuous Flow Centrifugation:

To evaluate the option of continuous centrifugation in a pilot scale, softwood condensates and RO retentate were processed through a Westfalia continuous flow centrifuge at 800 mL/min, spinning at approximately 12,000 rpm.

Figure 12A:
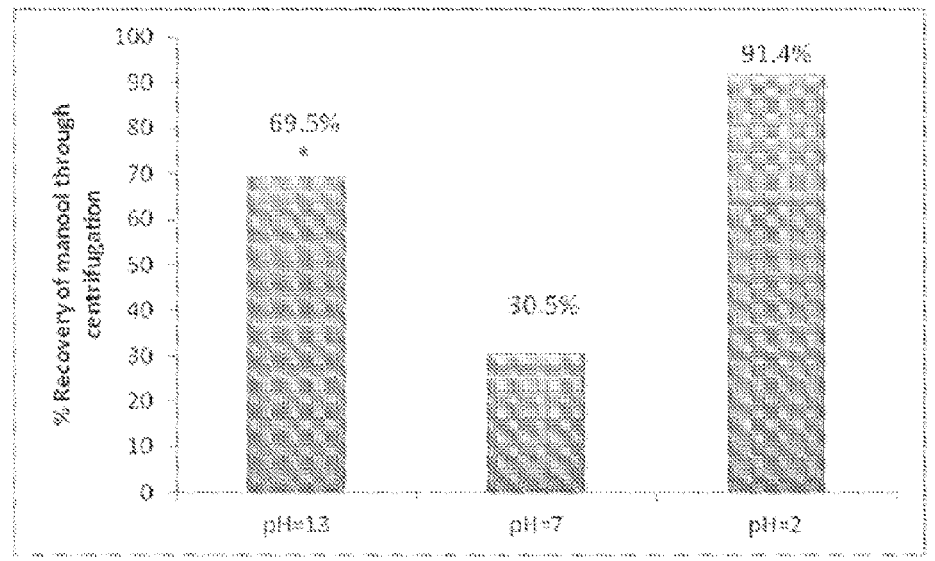
FIGS. 12A-12B show the results of recovering manool by pilot scale continuous flow centrifugation at different pH's.
Figure 12B:
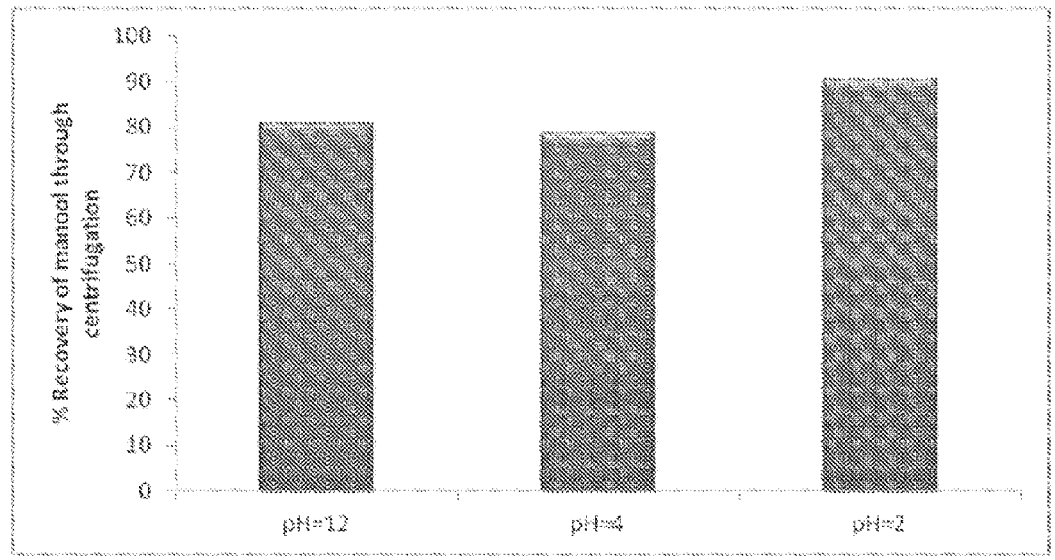

Condensates were processed at pH 12 (ambient), pH 7 and pH 2, and RO retentate samples were processed at pH 13 (ambient), pH 4 and pH 2. The highest solids and manool recovery was found at pH 2 (FIGS. 12A and 12B).

All solids recovered by centrifugation were found to be completely soluble in methanol or ethyl acetate, either of which is useful for further processing (e.g. by distillation). Both solvents are also suitable for various industrial applications, for example in the fragrance or food industries. Solids were also completely soluble in dichloromethane (DCM) and acetone, which is suitable for analytical purposes.

Solids recovered from pilot scale continuous flow centrifuging of RO retentate adjusted to pH 2 were dried in a dessicator overnight and extracted with toluene. Toluene was used as solvent for convenience, as this solvent was used for all GC work and avoided a solvent exchange step. Centrifuged solids were found to be 10.2±0.7% manool by dry weight.
Liquid-Liquid Extraction:
i) Batch Extraction and recovery using heptane, ethyl acetate, dichloromethane (DCM) and methyl-t-butyl ether (MTBE) was evaluated at pH 2 for 2 hours.

Figure 13A:
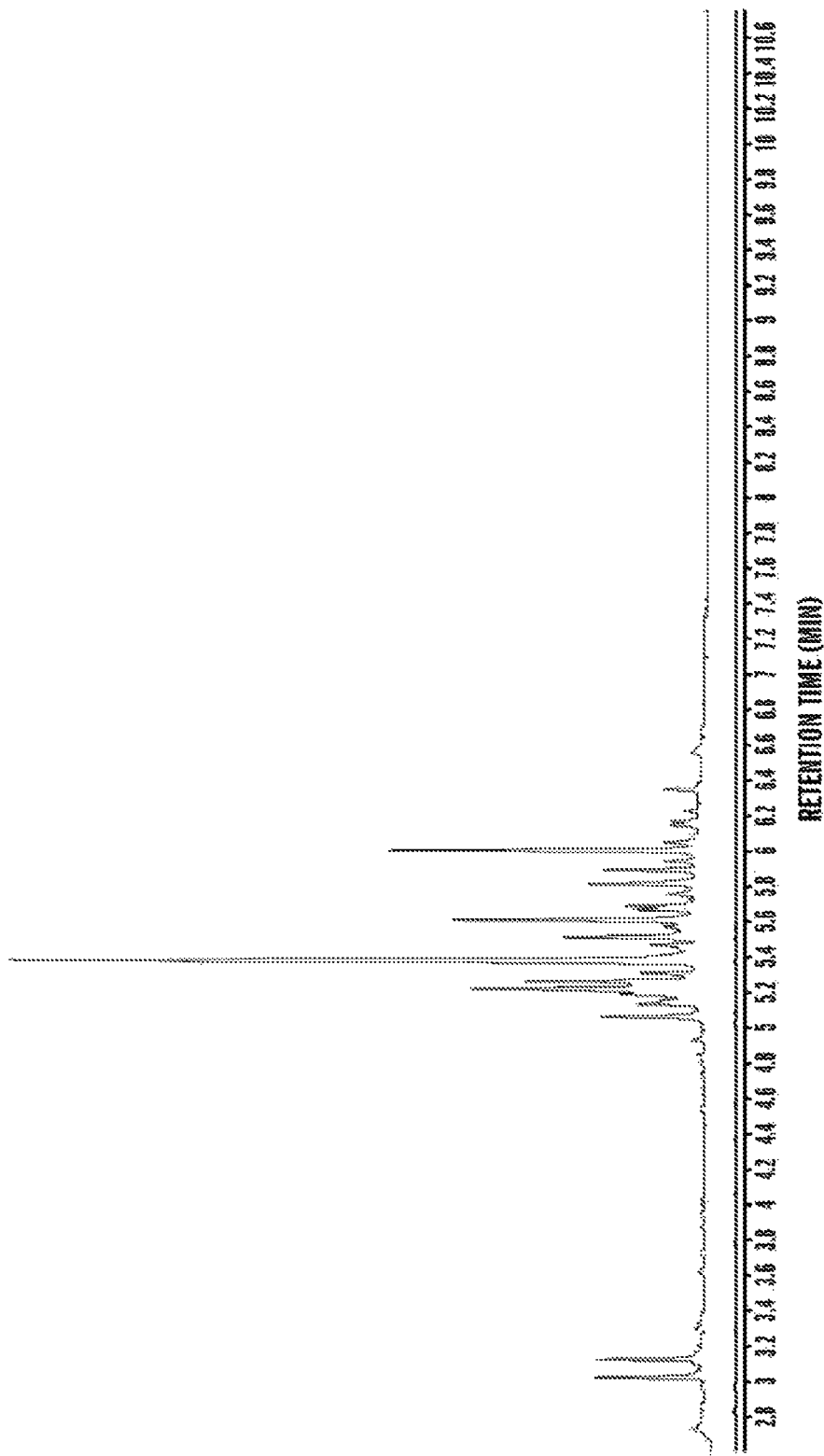
FIGS. 13A and 13B show total ion chromatograms of GC-MS full scan analyses of softwood 5th effect condensate (Conditions: unit mass resolution, scanning m/z 50-550, electron impact ionization).
Figure 13B:
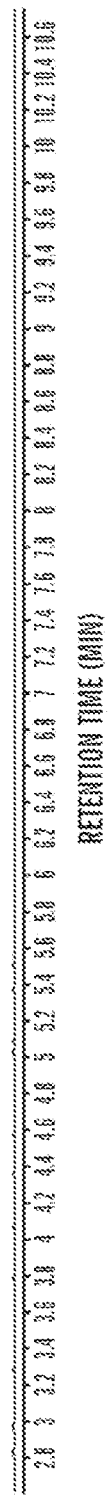
Figure 14:
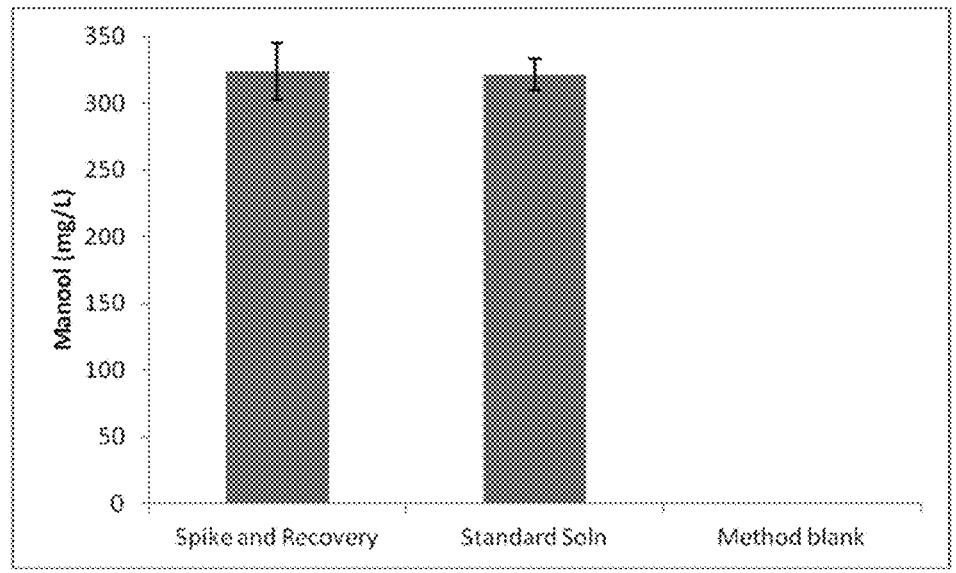
FIG. 14 illustrates spike and recovery data from monitoring experiments, showing recovery after spike and recovery extracting manool from water using ethyl acetate. Results reflect 100% recovery of manool from spiked water. Error bars are standard deviation of analyses conducted in triplicate.

DCM, heptane and MTBE created emulsions and were therefore discontinued. However, ethyl acetate had the least emulsions of all solvents and it was found that >99% manool recovery and excellent recovery of organics (as detected by GC-MS) could be obtained with vigorous agitation (FIGS. 13A and 13B). In addition, spike and recovery extraction of manool from water using ethyl acetate at pH 2 gave 100.6±7% recovery using a 1:1 solvent ratio (FIG. 14).

Solvent ratios using ethyl acetate was further evaluated for optimization of compound recovery (Table 5), and it was determined that manool is recovered adequately with an ethyl acetate ratio as low as 0.2:1 (20% v/v), with adequate mixing.

In addition, extraction time for compound recovery was evaluated. As demonstrated in Table 6, manool is extracted almost instantly with ethyl acetate under the tested conditions (2×10 s extractions).

TABLE 5

Optimization of solvent ratio for manool recovery in batch liquid-liquid extractions. All extractions conducted using ethyl acetate with condensates adjusted to pH 2. Two sequential extractions were conducted with vigorous stirring, each for 1 hour.

| Solvent:Condensate ratio (volume) | Recovery following $1^{st}$ extraction (%) | Recovery following $2^{nd}$ extraction (%) | Total Recovery (%) |
|---|---|---|---|
| 1:1 | 91.9 ± 5.1 | 7.8 ± 3.8 | 99.6 |
| 0.5:1 | 83.4 ± 11.5 | 14.8 ± 8.5 | 98.2 |
| 0.2:1 | 74.7 ± 13.3 | 23.2 ± 18.5 | 97.9 |

TABLE 6

Optimization of extraction time for manool recovery in batch liquid-liquid extractions. All extractions conducted using ethyl acetate and condensates adjusted to pH 2 (solvent ratio of 0.5:1). Two sequential extractions were conducted with vigorous stirring, each for the time specified.

| Solvent extraction time | Recovery following 1st extraction (%) | Recovery following 2nd extraction (%) | Total Recovery (%) |
|---|---|---|---|
| 10 seconds | 79.6 ± 9.2 | 16.2 ± 0.9 | 95.8 |
| 1 minute | 80.3 ± 4.4 | 17.5 ± 7.5 | 97.8 |
| 5 minutes | 81.0 ± 6.5 | 13.6 ± 5.1 | 94.6 |
| 10 minutes | 79.6 ± 5.8 | 17.2 ± 1.2 | 96.8 |

Extracts were dried using sodium sulfate to remove water for analytical purposes (GC-MS).

ii) Continuous

Extraction and recovery using heptane and ethyl acetate was evaluated singly and in sequence, at different pH's (pH 12 and pH 2) and for different extraction times (12 and 72 hours duration). The results of these optimization studies are shown in Tables 6-11. It was found through these studies that additional agitation gave enhanced recovery, reduced emulsion formation and reduced extraction time.

TABLE 7

Condensate and RO retentate adjusted to pH <2 and extracted with ethyl acetate for 18 hours, continuous liquid-liquid extraction

| | | Pre-extraction (mg/L) | Post-extraction (mg/L) | Extraction efficiency (%) |
|---|---|---|---|---|
| Softwood | Retentate | 1170 | 0.38 | 99.9 |
| | Condensate | 45 | * | |
| Hardwood | Retentate | 194 | 0.95 | 99.5 |
| | Condensate | 3.9 | * | |

TABLE 8

Sequential extraction of Softwood and Hardwood RO Retentates at pH = 2 using i) heptane first followed by ii) ethyl acetate.

| | Softwood Retentate (% extracted) | Hardwood Retentate (% extracted) |
|---|---|---|
| Heptane | 60.8 | 46.8 |
| Ethyl acetate | 39.2 | 53.2 |
| Overall Extraction efficiency* | 99.99% | 99.95% |

*based on measured concentration of manool remaining in water following extraction.

TABLE 9

Non-pH adjusted (with subsequent pH adjustment <2) liquid-liquid extraction of softwood condensate (pH = 11.8) and RO retentate (13.1).

| | Retentate (% Manool recovered) | Condensate (% Manool recovered) |
|---|---|---|
| Heptane 1 | 43.3 | 53.1 |
| Heptane 2 | 19.4 | 21.3 |
| Ethyl Acetate 1 | $10.7^a$ | $25.7^b$ |
| Ethyl Acetate 2 (pH <2) | 26.4 | 0.1 |
| Heptane 3 (pH <2) | 0.2 | 0.2 |

$^a$pH = 7.9 following first ethyl acetate extraction.
$^b$pH = 6.5 following first ethyl acetate extraction.

TABLE 10 pH adjusted liquid-liquid extraction of softwood RO retentate (all pH <2).

| | Retentate (%) |
|---|---|
| Heptane 1 | 18.3 |
| Heptane2 | 3.3 |
| Ethyl Acetate | 78.3 |

TABLE 11

Non pH adjusted (with later pH adjustment) of hardwood retentate (pH = 12.7) and condensate (pH = 11.5).

| | Retentate (%) | Condensate (%) |
|---|---|---|
| Heptane 1 | 8.7 | 57.0 |
| Heptane 2 | 14.5 | 26.3 |
| Ethyl Acetate 1 | $56.0^a$ | 13.8 |
| Ethyl Acetate 2 (after pH drop <2) | 20.8 | 2.8 |

$^a$pH was 8.0 after first ethyl acetate extraction.
$^b$pH was 6.3 after first ethyl acetate extraction.

Example 5

Purification

Purification of target compounds may be carried out as described above. For instance, purification by high pressure liquid chromatography (HPLC) was used in Example 2 to obtain manool with 60% purity. Other techniques may also be used, including but not limited to simple, fractionation, vacuum or steam distillation techniques. For isolation method development vacuum distillation of the crude extracts is being evaluated. Both batch and continuous distillation methods are envisioned.

As an example of a vacuum distillation procedure, a vacuum still equipped with a still pot can be used. The pot can be glass lined and jacketed for steam heating and tap water cooling. An agitation device (e.g. a mechanically driven propeller) can be positioned in the pot. A fractionating column as well as an adjustable reflux apparatus can be used.

A quantity of organic extract in the appropriate solvent, e.g. ethyl acetate, is charged into the pot at, e.g. 8 mm absolute pressure at zero time and at approximately 29° C., and heat applied. When liquid is noted in the reflux glass, samples can be collected with fractions of desired volumes and collected throughout the duration of the distillation process. Components with low boiling components will volatize and be collected in the initial fractions, and components with higher boiling points will separate and be collected in later fractions. Purity measurements can be conducted using full scan GC-MS and NMR.

Example 6

Monitoring

All manool measurements were conducted using a newly developed GC-MS-MS multiple-reaction-monitoring method.

Monitoring of manool contents in condensates and RO retentate was carried out over the course of an entire batch-based production cycle (hardwood, switchover, softwood) at a kraft mill. Extensive matrix characterization of both condensates and RO retentate was conducted. Measurements of additional extractives was also included. Manool and other extractives were analyzed in effluent samples from 2 additional Canadian mills and 2 Brazilian mills for comparison of results to the overall pulp and paper industry.

i) Canadian Kraft Mill Pulping Softwood/Hardwood Batches:

Monitoring was carried out at a Canadian kraft mill equipped with a reverse osmosis (RO) system on the 5th effect evaporator, which dewaters 5th effect condensates for BOD reduction.

Manool and other known extractives were monitored daily in 5th effect condensates prior to RO, and in the RO retentate product stream throughout a complete cycle of hardwood to softwood batch production, including changeovers. Softwood production was derived from a mix of feedstocks: 65% spruce, 30% fir, 5% pine. Hardwood production was derived from a feedstock of 90% maple with a softwood mix of 10%.

Figure 15A:
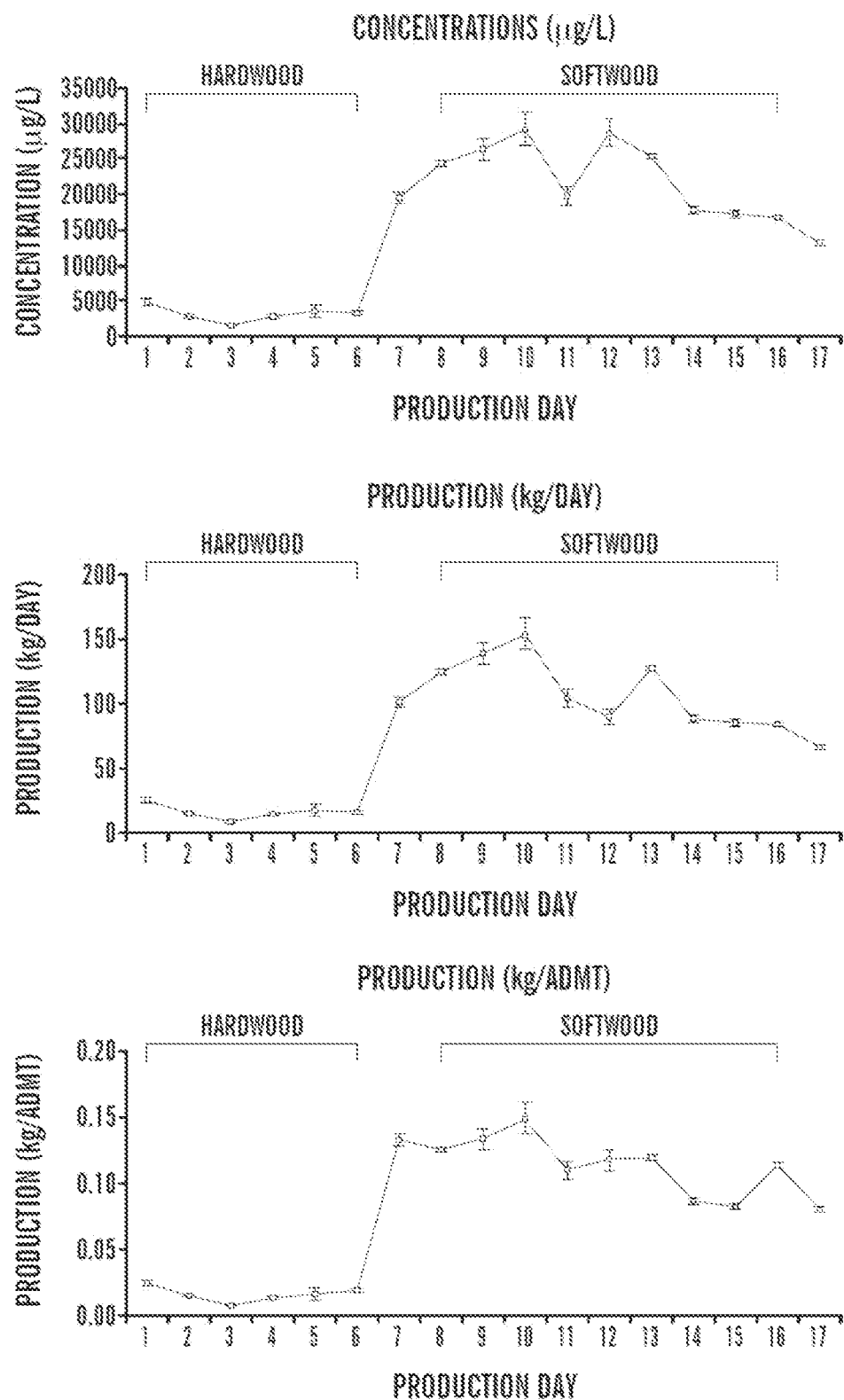
FIGS. 15A and 15B show manool concentrations and production rates in (FIG. 15A) 5th effect condensates and (FIG. 15B) RO retentate during an entire production cycle at a Canadian kraft mill equipped with an RO system on the 5th effect evaporator. Error bars are standard deviation of analyses conducted in triplicate.
Figure 15B:
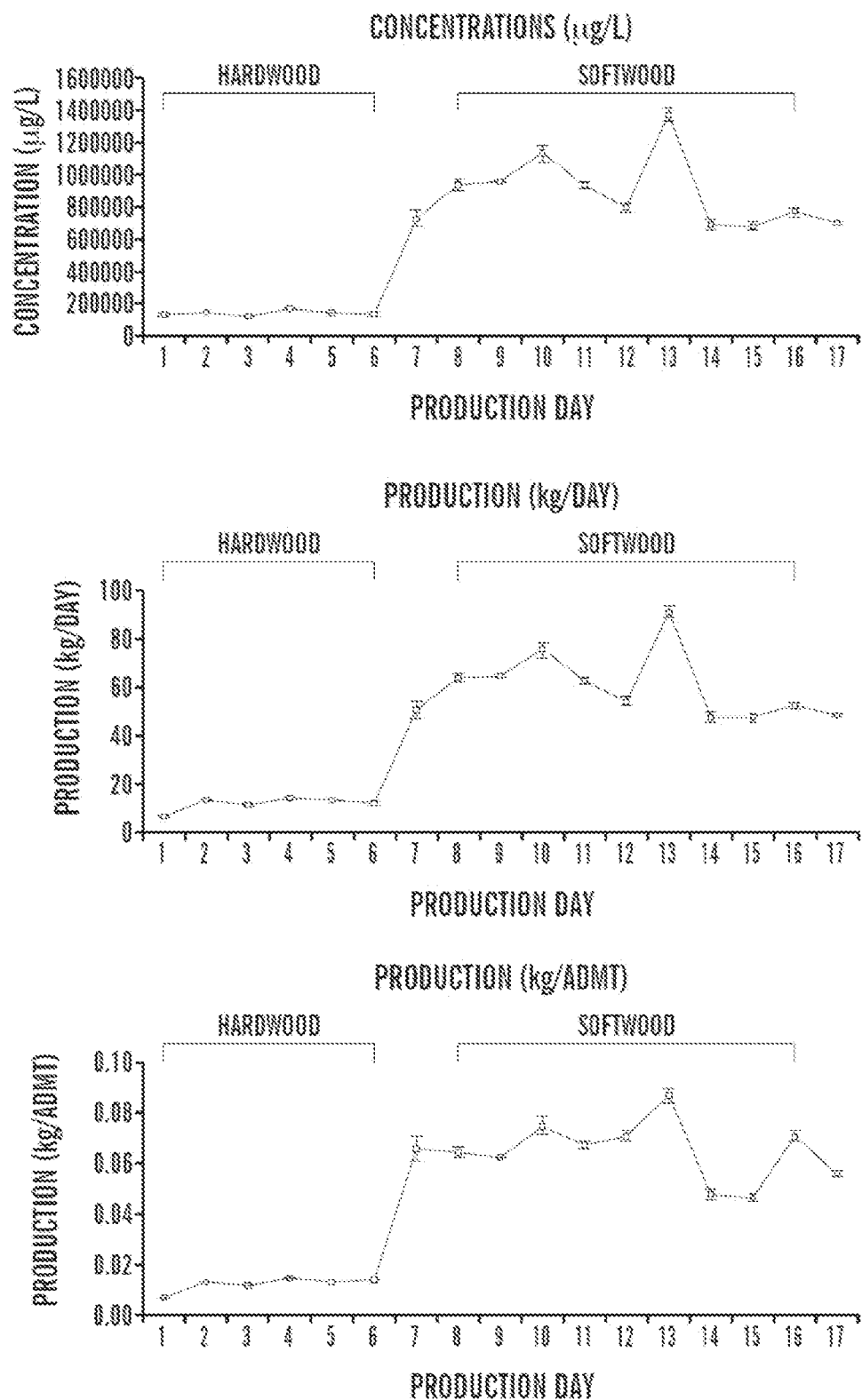

As illustrated in FIG. 15, results show manool is strongly associated with softwood pulping, since manool production rises immediately after switching from hardwood to softwood. The hardwood production at this mill contains 10% softwood, therefore manool appears to be associated with softwood production only and not in the hardwood varieties present in the feedstock at this particular mill.

The average manool production from the softwood derived condensates at this mill was 110.8 kg/day, or 0.115 kg/ADMT (ADMT represents Air Dried Metric Tonne of pulp). By comparison, the average manool production from the softwood derived retentates at this mill was 60.0 kg/day; 0.063 kg/ADMT. This evidence suggests that enhanced recovery of manool can be obtained if samples are taken upstream of a RO system installed at a mill.

Additional compounds other than manool were also monitored in the softwood derived condensates and RO retentates at this mill. The results are shown in Tables 12 and 13 for a selection of the compounds known to be present in these extracts. In addition, the elemental composition of the extracts were determined and are shown in Tables 14 and 15.

TABLE 12

Concentrations of other confirmed extractives in ECF kraft 5th effect condensates from the monitoring study described above. All concentrations determined by GC-MS-MS.

| | Concentration (mg/L) | | | |
| | Hardwood | | Softwood | |
| Compound | Avg | SD | Avg | SD |
| --- | --- | --- | --- | --- |
| trans-terpin | ND | — | 2.05 | 1.11 |
| geranyl linalool | 4.34 | 0.90 | 32.34 | 4.51 |
| squalene | 1.35 | 1.11 | 0.031 | 0.092 |

TABLE 13

Concentrations of other confirmed extractives in RO retentate derived from ECF kraft 5th effect condensates from the monitoring study described above. All concentrations determined by GC-MS-MS.

| | Concentration (mg/L) | | | |
| | Hardwood | | Softwood | |
| Compound | Avg | SD | Avg | SD |
| --- | --- | --- | --- | --- |
| trans-terpin | 15,006 | 4,203 | 0.25 | 0.13 |
| geranyl linalool | 178 | 24 | ND | — |
| 4-ethylguaiacol | 100 | 22 | 0.054 | 0.016 |

TABLE 14

Matrix composition of Canadian ECF kraft $5^{th}$ effect condensates prior to extraction, from monitoring study.

| | | Detection | Hardwood | | Softwood | |
| Element | Units | Limits | Avg | SD | Avg | SD |
| --- | --- | --- | --- | --- | --- | --- |
| Bromide by IC | mg/L | 0.067 | ND | | ND | |
| Chloride by IC | mg/L | 0.032 | 0.60 | 0.74 | 0.21 | 0.10 |
| Dissolved Inorganic Carbon | mg/L | 0.253 | 2.78 | 1.39 | 2.32 | 1.29 |
| Dissolved Organic Carbon | mg/L | 0.253 | 91.91 | 20.47 | 116.10 | 13.09 |
| Fluoride by IC | mg/L | 0.054 | 0.55 | 0.71 | 0.60 | 0.73 |
| NO3 as N by IC | mg/L | 0.021 | ND | | ND | |
| PO4 as P by IC | mg/L | 0.071 | ND | | 0.30 | 0.10 |
| Total Inorganic Carbon in Water | mg/L | 0.253 | 2.46 | 1.06 | 2.45 | 1.24 |
| Total Organic Carbon | mg/L | 0.253 | 119.29 | 43.96 | 210.40 | 25.69 |

TABLE 14-continued

Matrix composition of Canadian ECF kraft 5th effect condensates prior to extraction, from monitoring study.

| Element | Units | Detection Limits | Hardwood Avg | Hardwood SD | Softwood Avg | Softwood SD |
|---|---|---|---|---|---|---|
| Calcium (dissolved) | ug/L | 5.45 | 787.57 | 289.74 | 570.90 | 180.94 |
| Silver (dissolved) | ug/L | 0.296 | ND | | ND | |
| Silver (total) | ug/L | 0.296 | 0.93 | 0.41 | ND | |
| Aluminum (dissolved) | ug/L | 0.142 | 132.07 | 65.69 | 139.29 | 52.50 |
| Aluminum (total) | ug/L | 0.142 | 108.86 | 46.12 | 70.75 | 47.31 |
| Boron (dissolved) | ug/L | 0.371 | ND | | 179.59 | 130.76 |
| Beryllium (dissolved) | ug/L | 0.105 | ND | | ND | |
| Beryllium (total) | ug/L | 0.105 | ND | | ND | |
| Boron (total) | ug/L | 0.371 | ND | | ND | |
| Calcium (total) | ug/L | 5.45 | 717.14 | 223.63 | 451.90 | 152.76 |
| Cobalt (dissolved) | ug/L | 0.133 | ND | | ND | |
| Cobalt (total) | ug/L | 0.133 | ND | | ND | |
| Chromium (dissolved) | ug/L | 0.135 | 0.83 | 0.43 | 0.72 | 0.48 |
| Chromium (total) | ug/L | 0.135 | 1.08 | 0.45 | 0.79 | 0.32 |
| Copper (dissolved) | ug/L | 0.556 | 16.10 | — | 16.00 | 25.59 |
| Copper (total) | ug/L | 0.556 | 1.52 | 1.73 | 1.69 | 2.45 |
| Iron (dissolved) | ug/L | 1.41 | 61.07 | 33.67 | 44.64 | 17.07 |
| Iron (total) | ug/L | 1.41 | 92.16 | 45.25 | 63.13 | 26.48 |
| Potassium (dissolved) | ug/L | 1.76 | 2332.71 | 2449.92 | 2879.00 | 1893.16 |
| Potassium (total) | ug/L | 1.76 | 1996.71 | 2210.36 | 2316.10 | 1332.62 |
| Lithium (dissolved) | ug/L | 0.11 | ND | | ND | |
| Lithium (total) | ug/L | 0.11 | ND | | ND | |
| Magnesium (dissolved) | ug/L | 0.097 | 125.56 | 76.91 | 97.05 | 34.76 |
| Magnesium (total) | ug/L | 330 | ND | | ND | |
| Manganese (dissolved) | ug/L | 0.079 | 10.14 | 13.19 | 12.63 | 7.27 |
| Manganese (total) | ug/L | 0.079 | 10.76 | 13.86 | 13.25 | 8.95 |
| Sodium (diss.) | ug/L | 0.553 | 74342.86 | 30453.78 | 48020.00 | 17583.57 |
| Sodium (total) | ug/L | 0.553 | 69280.00 | 35918.44 | 45820.00 | 16359.35 |
| Nickel (dissolved) | ug/L | 0.28 | 0.64 | 0.34 | 0.43 | #DIV/0! |
| Nickel (total) | ug/L | 0.28 | 1.98 | 1.24 | 1.19 | 0.97 |
| Lead (dissolved) | ug/L | 1.98 | ND | | ND | |
| Lead (total) | ug/L | 1.98 | ND | | ND | |
| S dissolved in water by ICP | ug/L | 4.44 | 20828.57 | 4416.15 | 17930.00 | 6065.21 |
| Silicon (dissolved) | ug/L | 3.85 | 2922.86 | 1009.07 | 1838.50 | 681.30 |
| Silicon (total) | ug/L | 3.85 | 2285.71 | 605.03 | 3225.10 | 4989.80 |
| Sulfur (total) | ug/L | 4.44 | 16131.43 | 5694.52 | 15710.00 | 2559.71 |
| Titanium (dissolved) | ug/L | 1.15 | 507.27 | 710.97 | 1.22 | #DIV/0! |
| Titanium (total) | ug/L | 1.15 | 6.89 | 8.15 | 1.63 | 0.49 |
| Zinc (dissolved) | ug/L | 0.105 | 31.25 | 21.45 | 228.07 | 210.65 |
| Zinc (total) | ug/L | 0.105 | 732.61 | 1890.73 | 28.63 | 69.96 |

TABLE 15

Matrix composition of Canadian ECF kraft RO Retentate corresponding to condensates in Table 14.

| Element | Units | Detection Limits | Hardwood Avg | Hardwood SD | Softwood Avg | Softwood SD |
|---|---|---|---|---|---|---|
| Bromide by IC | mg/L | 0.067 | 3.78 | 3.17 | 8.47 | 6.52 |
| Chloride by IC | mg/L | 0.032 | 43.10 | 13.99 | 30.54 | 15.42 |
| Dissolved Inorganic Carbon | mg/L | 0.253 | 24.02 | 11.44 | 32.77 | 14.20 |
| Dissolved Organic Carbon | mg/L | 0.253 | 2007.14 | 556.02 | 3270.00 | 916.55 |
| Fluoride by IC | mg/L | 0.054 | 13.82 | 8.62 | 26.87 | 12.53 |
| NO3 as N by IC | mg/L | 0.021 | ND | | ND | |
| PO4 as P by IC | mg/L | 0.071 | 2.99 | 2.08 | 2.53 | 1.89 |
| Total Inorganic Carbon in Water | mg/L | 0.253 | 16.06 | 13.05 | 30.55 | 11.78 |
| Total Organic Carbon | mg/L | 0.253 | 2925.71 | 1777.40 | 7048.00 | 3089.10 |
| Calcium (dissolved) | ug/L | 5.45 | 1998.57 | 378.52 | 1980.00 | 470.41 |
| Silver (dissolved) | ug/L | 0.296 | ND | | ND | |
| Silver (total) | ug/L | 0.296 | ND | | ND | |
| Aluminum (dissolved) | ug/L | 0.142 | 268.43 | 20.00 | 248.80 | 54.87 |
| Aluminum (total) | ug/L | 0.142 | 309.29 | 84.84 | 339.90 | 145.28 |
| Boron (dissolved) | ug/L | 0.371 | 85.50 | 42.97 | 117.07 | 95.53 |
| Beryllium (dissolved) | ug/L | 0.105 | ND | | ND | |
| Beryllium (total) | ug/L | 0.105 | ND | | ND | |
| Boron (total) | ug/L | 0.371 | ND | | ND | |
| Calcium (total) | ug/L | 5.45 | 1892.86 | 353.87 | 1751.00 | 487.25 |

TABLE 15-continued

Matrix composition of Canadian ECF kraft RO Retentate corresponding to condensates in Table 14.

| Element | Units | Detection Limits | Hardwood Avg | SD | Softwood Avg | SD |
|---|---|---|---|---|---|---|
| Cobalt (dissolved) | ug/L | 0.133 | ND | | ND | |
| Cobalt (total) | ug/L | 0.133 | ND | | ND | |
| Chromium (dissolved) | ug/L | 0.135 | ND | | ND | |
| Chromium (total) | ug/L | 0.135 | 2.79 | 3.65 | 0.84 | 0.38 |
| Copper (dissolved) | ug/L | 0.556 | ND | | ND | |
| Copper (total) | ug/L | 0.556 | ND | | ND | |
| Iron (dissolved) | ug/L | 1.41 | 153.20 | 58.04 | 150.44 | 60.33 |
| Iron (total) | ug/L | 1.41 | 303.14 | 121.52 | 284.40 | 109.60 |
| Potassium (dissolved) | ug/L | 1.76 | 27772 | 17102 | 48230 | 18230 |
| Potassium (total) | ug/L | 1.76 | 24637 | 14365.73 | 39580.00 | 15812.92 |
| Lithium (dissolved) | ug/L | 0.11 | ND | | ND | |
| Lithium (total) | ug/L | 0.11 | ND | | ND | |
| Magnesium (dissolved) | ug/L | 0.097 | 458.00 | 172.03 | 662.00 | 191.19 |
| Magnesium (total) | ug/L | 330 | 453.14 | 179.85 | 635.30 | 200.56 |
| Manganese (dissolved) | ug/L | 0.079 | 250.23 | 133.39 | 459.20 | 137.02 |
| Manganese (total) | ug/L | 0.079 | 254.74 | 142.92 | 454.00 | 147.94 |
| Sodium (diss.) | ug/L | 0.553 | 2005714 | 327508 | 1205500 | 409592 |
| Sodium (total) | ug/L | 0.553 | 1952857 | 311753 | 1150500 | 383986 |
| Nickel (dissolved) | ug/L | 0.28 | 5.42 | | ND | |
| Nickel (total) | ug/L | 0.28 | 4.21 | 4.17 | 10.84 | 11.11 |
| Lead (dissolved) | ug/L | 1.98 | ND | | ND | |
| Lead (total) | ug/L | 1.98 | ND | | ND | |
| S dissolved in water by ICP | ug/L | 4.44 | 387142 | 161687 | 232400 | 42392 |
| Silicon (dissolved) | ug/L | 3.85 | 8952 | 1858 | 11266 | 3467 |
| Silicon (total) | ug/L | 3.85 | 7502 | 1447 | 8870 | 2664 |
| Sulfur (total) | ug/L | 4.44 | 522285 | 127476 | 505200 | 140111 |
| Titanium (dissolved) | ug/L | 1.15 | ND | | ND | |
| Titanium (total) | ug/L | 1.15 | 10.19 | 8.94 | 11.02 | 7.96 |
| Zinc (dissolved) | ug/L | 0.105 | 574.14 | 50.24 | 469.00 | 70.53 |
| Zinc (total) | ug/L | 0.105 | 45.74 | 11.74 | 32.68 | 8.39 | ii) Data from Other Mills:

Monitoring was also carried out on samples obtained from pulp and paper waste streams derived from other Canadian and foreign mills.

As is evident from the results in Table 16, manool is present in waste streams in each of the tested Canadian and Brazilian mills, including feedstocks of both softwood and hardwood varieties (spruce, fir, pine, birch, poplar and *eucalyptus* varieties). The elemental composition of the extracts derived from these mills were also determined and are shown in Table 17.

TABLE 16

Additional sources of manool and estimated production from Canadian and Brazilian pulp and paper mill waste streams. Manool was the most abundant compound based on GC-MS in all samples.

| Mill sampled | Feedstock | Process stream sampled | Flow rate | Manool Concentration | Estimated production (kg/day) |
|---|---|---|---|---|---|
| Canadian ECF kraft mill from above | softwood, typically 65% spruce 30% fir 5% pine | 5$^{th}$ effect chemical recovery condensates | 2.9 m$^3$/min | 22.95 mg/L | 110.8 |
| Canadian unbleached thermomechanical mill | Softwood 85% spruce 15% Balsam fir | Final effluent | 0.336 m$^3$/s | 14.2 ug/L | 0.413 |
| Canadian neutral sulfite semi-chemical mill (30% recycled) | Hardwood 50% birch 25% poplar 25% others | Heat recovery condensates | 100-500 gpm or 454-2273 L/min | 1730 ug/L | 1.1-5.7 |
| Canadian neutral sulfite semi-chemical mill (30% recycled) | Hardwood 50% birch 25% poplar 25% others | Final effluent | 180-200 m$^3$/h | 634 ug/L | 2.9 |
| Brazilian ECF kraft | Softwood 100% *Pinus radiata* | 5$^{th}$ effect chemical recovery condensates | 160-170 m$^3$/h | 511 ug/L | 2.0 |

TABLE 16-continued

Additional sources of manool and estimated production from Canadian and Brazilian pulp and paper mill waste streams. Manool was the most abundant compound based on GC-MS in all samples.

| Mill sampled | Feedstock | Process stream sampled | Flow rate | Manool Concentration | Estimated production (kg/day) |
|---|---|---|---|---|---|
| Brazilian ECF kraft | Hardwood 100% Eucalyptus globulus | 5$^{th}$ effect chemical recovery condensates | 15 m$^3$/h | 75 ug/L | 0.027 |

TABLE 17

Matrix compositions of effluents from Canadian and Brazilian mills where the extraction method has been validated. Manool was the most abundant compound based on GC-MS in all samples.

| Element | Units | Detection Limits | Canadian neutral sulfite semi-chemical Hardwood + 30% recycled Heat Recovery Condensates | Final effluent | Brazilian ECF kraft 5$^{th}$ effect chemical recovery condensates Pinus radiata | Eucalyptus globulus |
|---|---|---|---|---|---|---|
| Bromide by IC | mg/L | 0.067 | 9.83 | N.D. | N.D. | N.D. |
| Chloride by IC | mg/L | 0.032 | 78.6 | 56 | 0.099 | 1.49 |
| Dissolved Inorganic Carbon | mg/L | 0.253 | 6.76 | 730 | 6.68 | 4.44 |
| Dissolved Organic Carbon | mg/L | 0.253 | 3.17 | 1510 | 154 | 90.9 |
| Fluoride by IC | mg/L | 0.054 | N.D. | N.D. | N.D. | 11.3 |
| NO3 as N by IC | mg/L | 0.021 | 0.327 | 0.193 | N.D. | N.D. |
| PO4 as P by IC | mg/L | 0.071 | N.D. | N.D. | N.D. | N.D. |
| Total Inorganic Carbon in Water | mg/L | 0.253 | 10.7 | 772 | 6.97 | 6.03 |
| Total Organic Carbon | mg/L | 0.253 | 6630 | 1310 | 173 | 154 |
| Calcium (dissolved) | ug/L | 5.45 | 355000 | 83400 | 350 | 215 |
| Silver (dissolved) | ug/L | 0.296 | 11.5 | 5.14 | N.D. | N.D. |
| Silver (total) | ug/L | 0.296 | 16.7 | 12.2 | N.D. | N.D. |
| Aluminum (dissolved) | ug/L | 0.142 | 10200 | 6440 | 71.7 | 65 |
| Aluminum (total) | ug/L | 0.142 | 16300 | 6580 | 22.5 | 64.3 |
| Boron (dissolved) | ug/L | 0.371 | 3090 | 1800 | N.D. | N.D. |
| Beryllium (dissolved) | ug/L | 0.105 | N.D. | N.D. | N.D. | N.D. |
| Beryllium (total) | ug/L | 0.105 | N.D. | N.D. | N.D. | N.D. |
| Boron (total) | ug/L | 0.371 | 1730 | 1540 | N.D. | N.D. |
| Calcium (total) | ug/L | 5.45 | 35300 | 91600 | 93.1 | 294 |
| Cobalt (dissolved) | ug/L | 0.133 | 0.335 | 9.55 | N.D. | 0.23 |
| Cobalt (total) | ug/L | 0.133 | 7.69 | 12.4 | N.D. | N.D. |
| Chromium (dissolved) | ug/L | 0.135 | 26.3 | 22 | N.D. | N.D. |
| Chromium (total) | ug/L | 0.135 | 47.9 | 24.7 | N.D. | 0.428 |
| Copper (dissolved) | ug/L | 0.556 | 78 | 50.5 | N.D. | N.D. |
| Copper (total) | ug/L | 0.556 | 312 | 58.8 | N.D. | 1.57 |
| Iron (dissolved) | ug/L | 1.41 | 2150 | 2210 | 252 | 3.11 |
| Iron (total) | ug/L | 1.41 | 7480 | 2370 | 27.2 | 1590 |
| Potassium (dissolved) | ug/L | 1.76 | 1050000 | 92100 | 2180 | 1580 |
| Potassium (total) | ug/L | 1.76 | 108000 | 93400 | 1340 | 1900 |
| Lithium (dissolved) | ug/L | 0.11 | 36.6 | 28.5 | N.D. | N.D. |
| Lithium (total) | ug/L | 0.11 | 40.3 | 29 | N.D. | N.D. |
| Magnesium (dissolved) | ug/L | 0.097 | 25700 | 18500 | 51.2 | 69.7 |
| Magnesium (total) | ug/L | 330 | 27500 | 54.3 | 19.1 | 76.8 |
| Manganese (dissolved) | ug/L | 0.079 | 12000 | 1200 | 17 | 3.93 |
| Manganese (total) | ug/L | 0.079 | 12400 | 1300 | 5.18 | 22.7 |
| Sodium (diss.) | ug/L | 0.553 | 2090000 | 1780000 | 20400 | 10100 |
| Sodium (total) | ug/L | 0.553 | 2050000 | 1950000 | 9650 | 19400 |
| Nickel (dissolved) | ug/L | 0.28 | 17.9 | 19.1 | N.D. | N.D. |
| Nickel (total) | ug/L | 0.28 | 24.6 | 20.5 | N.D. | 0.725 |
| Lead (dissolved) | ug/L | 1.98 | 75.6 | 29.2 | N.D. | N.D. |
| Lead (total) | ug/L | 1.98 | 99.5 | 27.3 | N.D. | N.D. |
| S dissolved in water by ICP | ug/L | 4.44 | 684000 | 474000 | 27500 | 7220 |
| Silicon (dissolved) | ug/L | 3.85 | 5810 | 6340 | 148 | 192 |
| Silicon (total) | ug/L | 3.85 | 11700 | 7460 | 7180 | 169 |
| Sulfur (total) | ug/L | 4.44 | 710000 | 530000 | 137 | 12000 |
| Titanium (dissolved) | ug/L | 1.15 | 36.9 | 37.2 | N.D. | N.D. |
| Titanium (total) | ug/L | 1.15 | 96.1 | 41.5 | N.D. | N.D. |

TABLE 17-continued

Matrix compositions of effluents from Canadian and Brazilian mills where the extraction method has been validated. Manool was the most abundant compound based on GC-MS in all samples.

| | | | Canadian neutral sulfite semi-chemical Hardwood + 30% recycled Heat | | Brazilian ECF kraft 5th effect chemical recovery condensates | |
|---|---|---|---|---|---|---|
| Element | Units | Detection Limits | Recovery Condensates | Final effluent | *Pinus radiata* | *Eucalyptus globulus* |
| Zinc (dissolved) | ug/L | 0.105 | 701 | 692 | 44.1 | 49.4 |
| Zinc (total) | ug/L | 0.105 | 1810 | 292 | 2.7 | 8.4 |

All identified references are herein incorporated by reference.

One or more currently preferred embodiments have been described by way of example. It will be apparent to persons skilled in the art that a number of variations and modifications can be made without departing from the scope of the invention as defined in the claims.

REFERENCES

1. Belknap, A. M., K. R. Solomon, D. L. MacLatchy, M. G. Dubé, L. M. Hewitt. 2006. Identification of compounds associated with testosterone depressions in fish exposed to bleached kraft pulp and paper mill chemical recovery condensates. Environ. Toxicol. Chem. 25:2322-2333.
2. Dubé M. G., MacLatchy D. L. 2000. Reverse osmosis treatment of condensate from a bleached kraft pulp mill: Effects on acute and chronic toxicity of process streams and final effluent. Proceedings, 4th International Conference on Environmental Impacts of the Pulp and Paper Industry, Helsinki, Finland, June 12-15, pp270-276.
3. Dubé M. G., MacLatchy D. L. 2001. Identification and treatment of a waste stream at a bleached-kraft pulp mill that depresses a sex steroid in the mummichog (*Fundulus heteroclitus*). Environ Toxicol Chem 20:985-995.
4. Hewitt, L. M., S. A. Smyth, M. G. Dubé, C. I. Gilman, D. L. MacLatchy. 2002. Isolation of compounds from bleached kraft mill chemical recovery condensates associated with reduced levels of testosterone in mummichog (*Fundulus heteroclitus*). Environ. Toxicol. Chem. 21:1359-1367.
5. MacLatchy D. L., M. G. Dubé, L. M. Hewitt. 2001. Evaluating reverse osmosis treatment for removal of compounds from recovery condensates at a bleached kraft mill that affect fish hormone control. Proceedings, TAPPI 2001 International Environmental Health and Safety Conference, Charlotte, N.C., USA, April 22-25, p 14.
6. Milestone, C., D. MacLatchy, M. Hewitt. 2008. Determining biologically active components in kraft mill chemical recovery condensates. Presented at the 5th World Congress of the Society of Environmental Toxicology and Chemistry, Aug. 3-7, 2008, Sydney Australia.
7. Shaughnessy, K, S., A. M. Belknap, L. M. Hewitt, M. G. Dubé and D. L. MacLatchy. 2007. Effects of kraft pulp Mill condensates on plasma testosterone levels in mummichog (*Fundulus heteroclitus*). Ecotoxicol. Environ. Saf. 67: 140-148.
8. Leach et al., 1976, Toxic constituents in mechanical pulping effluents, TAPPI, 59:2, 129.
9. Martel et al., 1997, Source and identity of compounds in a thermomechanical pulp mill effluent inducing hepatic mixed-function oxygenase activity in fish. Environ. Toxicol. Chem. 16:2375-2383.

What is claimed is:

1. A process for enriching or isolating a target compound from pulp and paper waste water, said process comprising the steps of:
    obtaining a condensate from a recovery evaporator or a reverse osmosis (RO) retentate of condensates of a pulp and paper mill, or both, the condensate, retentate or both being substantially free of higher molecular weight cellulose and/or lignin and/or lignin-derived material,
    adjusting pH of the condensate, RO retentate or both to about pH 2.0, and
    extracting the condensate with an organic solvent by solid phase extraction (SPE), liquid-liquid extraction or solid-liquid extraction to produce an extract containing said target compound.

2. The process of claim 1, further comprising filtering or centrifuging the condensate or RO retentate to collect water insoluble material and extracting the insoluble material with said organic solvent.

3. The process of claim 1, wherein the target compound is selected from the group consisting of manool, geranyl linalool, ethyl guaiacol, eugenol, veratraldehyde, squalene, terpin, cholesterol, beta-sitosterol, campesterol, stigmasterol, stigmastenol, dehydroabietic acid and combinations thereof.

4. The process of claim 1, wherein the condensate is obtained from a $1^{st}$, $2^{nd}$, $3^{rd}$, $4^{th}$, $5^{th}$ or higher effect recovery evaporator.

5. The process of claim 1, wherein the condensate is obtained from a $5^{th}$ effect recovery evaporator.

6. The process of claim 1, wherein the condensate is a dewatered concentrated $5^{th}$ effect condensate.

7. The process of claim 1, wherein the pulp and paper mill incorporates a reverse osmosis system.

8. The process of claim 7, wherein the reverse osmosis retentate is obtained from the reverse osmosis system and extracted.

9. The process of claim 1, wherein the pulp and paper mill is a softwood mill.

10. The process of claim 1, wherein the pulp and paper mill processes softwood comprising pine, spruce or fir varieties, or a combination thereof, or hardwood varieties that include maple, birch, aspen and the *Eucalyptus* genus.

11. The process of claim 1, wherein the organic solvent is selected from the group consisting of dichloromethane (DCM), ethyl acetate, hexane, toluene, methyl t-butyl ether (MTBE), ethanol, methanol, isopropanol and combinations thereof.

12. The process of claim 1, wherein the organic solvent comprises ethyl acetate.

13. The process of claim 1, wherein the condensate or RO retentate is filtered or centrifuged and extracted by solid phase extraction (SPE) or solid-liquid extraction.

14. The process of claim 13, wherein the condensate or RO retentate is filtered through filter paper or a glass fiber filter, having a pore size of 0.22-8 μm.

15. The process of claim 13, wherein the filtered condensate or RO retentate is extracted using SPE and eluted with one or more solvents selected from dichloromethane (DCM), methanol, ethyl acetate, toluene, and hexane.

16. The process of claim 1, further comprising purifying the target compound from the extract by thermal fractionation, chromatographic separation, recrystallization, ion exchange, chelation, adsorption/desorption, lyophilization and sublimation or combinations thereof.

17. A process for enriching or isolating a target compound selected from the group consisting of manool, geranyl linalool, ethyl guaiacol, eugenol, veratraldehyde, squalene, terpin, cholesterol, beta-sitosterol, campesterol, stigmasterol, stigmastenol, dehydroabietic acid and combinations thereof, said process comprising the steps of:

obtaining a condensate from a recovery evaporator or a reverse osmosis (RO) retentate of condensates of a pulp and paper mill, or both, the condensate, retentate or both being substantially free of higher molecular weight cellulose and/or lignin and/or lignin-derived material, adjusting pH of the condensate, retentate or both to enhance precipitation of said at least one target compound, and centrifuging the condensate or RO retentate to collect water insoluble material and thereby enrich or isolate said target compound from said pulp and paper waste water.

18. The process of claim 17, further comprising extracting the condensate, retentate or both with an organic solvent by solid-liquid extraction to produce an extract containing said target compound.

19. The process according to claim 18, further comprising purifying the target compound from the extract by thermal fractionation, chromatographic separation, recrystallization, ion exchange, chelation, adsorption/desorption, lyophilization and sublimation or combinations thereof.

20. The process according to claim 18, wherein the target compound is manool.

* * * * *